US008428882B2

(12) United States Patent
Chiu et al.

(10) Patent No.: US 8,428,882 B2
(45) Date of Patent: Apr. 23, 2013

(54) METHOD OF PROCESSING AND/OR GENOME MAPPING OF DITAG SEQUENCES

(75) Inventors: Kuo Ping Chiu, Singapore (SG); Yijun Ruan, Singapore (SG); Chia Lin Wei, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 1971 days.

(21) Appl. No.: 11/151,591

(22) Filed: Jun. 14, 2005

(65) Prior Publication Data

US 2006/0281097 A1    Dec. 14, 2006

(51) Int. Cl.
*G01N 33/50* (2006.01)

(52) U.S. Cl.
USPC .......................................................... 702/19

(58) Field of Classification Search .................. None
See application file for complete search history.

(56) References Cited

U.S. PATENT DOCUMENTS

| 6,506,561 | B1 * | 1/2003 | Cheval et al. ........................ 435/6 |
| 6,816,867 | B2 * | 11/2004 | Jevons et al. .................. 707/102 |
| 2005/0059022 | A1 * | 3/2005 | Ruan et al. ........................ 435/6 |

FOREIGN PATENT DOCUMENTS

| WO | 03065146 A2 | 8/2003 |
| WO | 2004050918 A1 | 6/2004 |
| WO | WO 2005/026391 A1 | 3/2005 |
| WO | WO 2005/042781 A2 | 5/2005 |
| WO | WO 2006/031204 A1 | 3/2006 |

OTHER PUBLICATIONS

Saha et al. "Using the transcriptome to annotate the genome," Nature Biotechnology, May 2002, vol. 19, No. 5, pp. 508-512.*
Wei, Chia-Lin, "5' Long serial analysis of gene expression (LongSAGE) and 3' LongSAGE for transcriptome characterization and genome annotation," *PNAS*, Aug. 10, 2004, pp. 11701-11706, vol. 101, No. 32.
Ng, W.P., et al., "Gene Identification Signature (GIS) Analysis: Detailed Potocol," *GIS Analysis Protocol*, Release NM091204:1-14, 2004.
Ng, P., et al., "Gene Identification (GIS) Analysis for Transcriptome Characterization and Genome Annotation," *Nature Methods*, Feb. 2005, pp. 105-111, vol. 2, No. 2.
Peters, B.A. et al., "Transcriptome PETs: A genome's best friends," *Nature Methods*, Feb. 2005, pp. 93-94, vol. 2, No. 2.
Margulies E.H. et al., "eSAGE: Managing and analysing data generated with serial analysis of gene expression (SAGE)", Bioinformatics, 16(7):650-651 (2000).
van Kampen A.H.C. et al., "Usage: A web-based approach towards the analysis of SAGE data", Bioinformatics, 16(10):899-905 (2000).
Keime C. et al., "Identitag, a relational database for SAGE tag identification and interspecies comparison of SAGE libraries", Bioinformatics, 5(1):143 (12 pages) (2004).

* cited by examiner

*Primary Examiner* — Jason Sims
(74) *Attorney, Agent, or Firm* — Rothwell, Figg, Ernst & Manbeck PC

(57) ABSTRACT

There is provided a method and system for processing and/or mapping ditag nucleotide sequence(s) to a genome, the ditag sequence comprising the 5' terminal tag and the 3' terminal tag of a nucleic acid molecule or fragment thereof or genomic fragment. The method of processing comprises preparing a database or file comprising at least one ditag sequence. The method of mapping comprises preparing a database or file of ditag(s), and mapping the ditag sequence(s) to the genome, comprising matching the 5' and the 3' terminal tags of the ditag sequence to at least a portion of the genome.

18 Claims, 20 Drawing Sheets

FIGURE 6

Algorithm Find_Sites (5' sites)
Input: A DNA segment P[1..m], a genome G[1..n], and a threshold *minlength$_5$* of minimum contiguous exact match.
Output: A set of 5' sites.

for i = *minlength$_5$* downto 1 do
Given the occurrence range of P[i+1..*minlength$_5$*], we find the occurrence
range of P[i..*minlength$_5$*] by Backward search (Lemma 2).
Extend and report all the occurrences of P[1..*minlength$_5$*]
for i = 2 to *boundary$_5$* - *minlength$_5$* + 1 do
for j= *minlength$_5$*+1 to i+*minlength$_5$*-1 do
Given the occurrence range of P[i..j-1], we find the occurrence range
of P[i..j] by Forward search (Lemma 1).
Extend and report all occurrences of P[i..i+*minlength$_5$*-1]

End Find_Sites (5' sites)

FIGURE 7

```
Algorithm Match_Sites_1
Input: A set of 5' sites and 3' sites.
Output: A set of occurring segments (feasible gene locations).

Sort the 5' sites in ascending order and let A[1], A[2], ..., A[p] be the list of 5' sites.
Sort the 3' sites in ascending order and let B[1], B[2], ..., B[q] be the list of 3' sites.
Let i=1 and j=1.
while (i ≤ p and j ≤ q) do
if (A[i]>B[j]) then
j = j + 1;
elseif (B[j]-A[i] ≤ maxlength)
report (A[i], B[j]) as an occurring segment and j=j+1;
else
i = i + 1;

End Match_Sites_1
```

FIGURE 8

Algorithm Match_Sites_2
Input: A set of 5' sites and 3' sites.
Output: A set of occurring segments.

Let i=1 and j=1.

if ($count_5$ << $count_3$) then
while (i ≤ p) do
    find 3' site located within *maxlength* downstream from A[i]
    report found 3' site and A[i] as an occurring segment
    i = i + 1;;
elseif ($count_5$ >> $count_3$)
while (j ≤ q) do
    find 5' site located within *maxlength* upstream from B[j]
    report found 5' site and B[j] as an occurring segment
    j = j + 1;;
else
    try Match_Sites_1

End Match_Sites_2

1. Project Module flow chart

2. Extractor Module Flow Chart

3. Examiner Module Flow Chart

4. Mapping Module Flow Chart

GISditagTool Examiner

Library List

C

| Library | Total Ditags | Unique Ditags | No of Good Reads | |
|---|---|---|---|---|
| test1 | 387815 | 266269 | 48706 | Export Ditags |
| SME005 | 139627 | 87502 | 22868 | Export Ditags |
| SME003_2 | 117082 | 63879 | 16547 | Export Ditags |
| sme003_241103 | 41692 | 31279 | 6158 | Export Ditags |
| SME003_2rerun | 116252 | 63467 | 16547 | Export Ditags |
| SME006 | 82431 | 41595 | 14708 | Export Ditags |
| SMN001 | 70310 | 51352 | 15236 | Export Ditags |
| SMT001 | 93429 | 45465 | 16717 | Export Ditags |
| MHF001 | 16 | 10 | 134 | Export Ditags |
| SHC003 | 512876 | 228845 | 77662 | Export Ditags |
| SHC002 | 1963 | 1876 | 386 | Export Ditags |
| SDE001 | 3718 | 3337 | 597 | Export Ditags |
| SDH001 | 0 | 0 | 0 | Export Ditags |
| Test_hg17 | 237 | 235 | 30 | Export Ditags |
| MoES_combine | 248234 | 135328 | 37754 | Export Ditags |

GISditagTool Examiner

Plate Statistics for MoES_combine

D

| | Plate | No of Good Reads | No of Ditags | Cumulative |
|---|---|---|---|---|
| Delete | ZZA10171T3 | 232 | 849 | 248234 |
| Delete | ZZA10170T3 | 265 | 910 | 247385 |
| Delete | ZZA10169T3 | 269 | 898 | 246475 |
| Delete | ZZA10168T3 | 215 | 854 | 245577 |
| Delete | ZZA10167T3 | 255 | 889 | 244723 |
| Delete | ZZA10166T3 | 237 | 936 | 243834 |
| Delete | ZZA10165T3 | 256 | 925 | 242898 |
| Delete | ZZA10164T3 | 337 | 2301 | 241973 |
| Delete | ZZA10163T3 | 326 | 2079 | 239672 |
| Delete | ZZA10162T3 | 319 | 2020 | 237593 |
| Delete | ZZA10161T3 | 341 | 2126 | 235573 |
| Delete | ZZA10160T3 | 313 | 1987 | 233447 |
| Delete | ZZA10159T3 | 333 | 2229 | 231460 |
| Delete | ZZA10158T3 | 333 | 2232 | 229231 |
| Delete | ZZA10157T3 | 325 | 2081 | 226999 |

FIGURE 19

Sequence: (462bp)

```
TGGTACCGAGCTCGGATCCGACTTGTGATTGAGATTTCTCGCCGAGACGTGACCCCTCGT    SEQ ID NO: 6
CGGATCCGACGCGAACGGCGAGCAGCGGCATAAAGTGATCTCGTTCAAGTCGGATCCGAC
GCTTCCCTTTAAGGGGGCGGCGTCCCTTCCTCATTAAGTCGGATCCGACTTAGATTTTTA
GAAATCAACGCACGCTGCACTCCCGCGTCGGATCCGACTTCCTTTTAAAATAATTTATGC
CGCCGCCGCTGCCCGTCGGATCCGACGTGGAAGAGGAGGAAACTTAGTTCGCTGCACCCA
CTAAGTCGGATCCGACTTGCAGTAACATTCCCGTTTTTCCTGCCTAAGCCGTCGGATCCG
ACGAGCGCCTTGGAGGTCCCAAGCTTTTTGAGACAGAAGTCGGATCCGACTTGGTGTTTG      F
CTTTTATTACCGCGCGCCCCAGACTCGTCGGATCCACTAGTA
```

| Sequence Type | Start | End | Length | Sequence | |
|---|---|---|---|---|---|
| Vector | 1 | 58 | 58 | TGGTACCGAGCTCGGATCCGACTTGTGATTGAGATTTCTCGCCGAGACGTGACCCCTC | SEQ ID NO: 7 |
| Spacer | 59 | 70 | 12 | GTCGGATCCGAC | SEQ ID NO: 3 |
| Ditag | 71 | 108 | 38 | GCGAACGGCGAGCAGCGGCATAAAGTGATCTCGTTCAA | SEQ ID NO: 8 |
| Spacer | 109 | 120 | 12 | GTCGGATCCGAC | SEQ ID NO: 3 |
| Ditag | 121 | 157 | 37 | GCTTCCCTTTAAGGGGGCGGCGTCCCTTCCTCATTAA | SEQ ID NO: 9 |
| Spacer | 158 | 169 | 12 | GTCGGATCCGAC | SEQ ID NO: 3 |
| Ditag | 170 | 206 | 37 | TTAGATTTTTAGAAATCAACGCACGCTGCACTCCCGC | SEQ ID NO: 10 |
| Spacer | 207 | 218 | 12 | GTCGGATCCGAC | SEQ ID NO: 3 |
| Ditag | 219 | 254 | 36 | TTCCTTTTAAAATAATTTATGCCGCCGCCGCTGCCC | SEQ ID NO: 11 |
| Spacer | 255 | 266 | 12 | GTCGGATCCGAC | SEQ ID NO: 3 |
| Ditag | 267 | 304 | 38 | GTGGAAGAGGAGGAAACTTAGTTCGCTGCACCCACTAA | SEQ ID NO: 12 |
| Spacer | 305 | 316 | 12 | GTCGGATCCGAC | SEQ ID NO: 3 |
| Ditag (Short) | 317 | 350 | 34 | TTGCAGTAACATTCCCGTTTTTCCTGCCTAAGCC | SEQ ID NO: 13 |
| Spacer | 351 | 362 | 12 | GTCGGATCCGAC | SEQ ID NO: 3 |
| Ditag | 363 | 398 | 36 | GAGCGCCTTGGAGGTCCCAAGCTTTTTGAGACAGAA | SEQ ID NO: 14 |
| Spacer | 399 | 410 | 12 | GTCGGATCCGAC | SEQ ID NO: 3 |
| Vector | 411 | 462 | 52 | TTGGTGTTTGCTTTTATTACCGCGCGCCCCAGACTCGTCGGATCCACTAGTA | SEQ ID NO: 15 |

METHOD OF PROCESSING AND/OR GENOME MAPPING OF DITAG SEQUENCES

FIELD OF THE INVENTION

The present invention relates to a method and system for processing ditag sequences. In particular, a method and system for preparing a database or file of ditag sequences. The present invention further provides a method and system for genome mapping of ditag sequences.

BACKGROUND OF THE INVENTION

Since the completion of the genome sequences for human and several other organisms, attention has been drawn towards annotation of genomes for functional elements including gene coding transcript units and regulatory cis-acting elements that modulate gene expression levels.

One of the major challenges is the identification of all genes and all transcripts expressed from the genes in human and model organisms. In the annotation of genes, full-length cDNA cloning and sequencing is the most conclusive and is viewed as the gold standard for the analysis of transcripts. However, this approach is expensive and slow when applied to a large number of transcripts across a large number of species and biological conditions. There are short tag based approaches such as SAGE (serial analysis of gene expression) and MPSS (massively parallel signature sequence). These short tag based methods extract a 14-20 bp signature for representing each transcript. The traditional SAGE approach, however, relies on the presence of restriction enzyme (RE) recognition sites, such as NlaIII, and lacks the capability of defining gene boundaries in the genome. Further, the specificity of the tags is often poor and the information yielded regarding transcript structures is frequently incomplete and ambiguous.

Gene Identification Signature (GIS) analysis, or Paired-End diTag (PET) analysis, is a new methodology which can precisely identify the transcription start sites (TSS) (also indicated as transcription initiation site (TIS)) and polyadenylation sites (PAS) of expressed genes in the genome to facilitate genome-wide transcriptome profiling (US 2005/0059022). The GIS (or PET) analysis was developed as a modification of the 5' LongSAGE (5'LS) and 3' LongSAGE (3'LS) analysis method (Wei, C-L., Ng, P., Chiu, K. P., Wong, C. H., Ang, C. C., Lipovich, L., Liu, E., and Ruan Y., 2004, 5' LongSAGE and 3' LongSAGE for transcriptome characterization and genome annotation. Proc. Natl. Acad. Sci. USA 101, 11701-11706). Starting with full-length cDNA clones, GIS links the first ~18 bp (5' tag) with the last ~18 bp (3' tag) of each full-length cDNA molecule in the same order and orientation—size variation is caused by the natural imprecision of TypeII restriction enzyme digestion—in such a way that the strand, order (5' followed by 3') and orientation are maintained. In such a way, libraries comprising GISditags (also referred to as PETs, GIS ditags or ditags) are prepared and sequenced. However, at present no efficient methods for the identification of GISditag sequences from these libraries, as well as the construction of GISditag databases, have been disclosed.

The GISditags are required to be mapped to find their corresponding genes on the genome. However, no mapping methods have been specifically disclosed for GISditags. Further, there are no existing computational algorithms that are readily applicable for mapping the GISditag sequences to the genome. In the past, SAGE and MPSS tags were matched to the tag-gene pairs in a virtual database generated from known sequences. With this approach, novel transcripts that did not exist in virtual databases would not be mapped. The two most often used sequence alignment tools are BLAST (basic local alignment search tool) and BLAT (BLAST-like alignment tool). However, they are not designed for short tag sequences. Further, BLAT often leads to poor or incorrect results, while BLAST requires a long time and is thus not suited for large-scale mapping.

There is therefore a need in this field of technology for new methods and systems for the organization and analysis of GISditag data, as well as efficient methods and systems for mapping ditags to genome.

SUMMARY OF THE INVENTION

The present invention addresses the problems above, and provides a new method and/or system of processing ditag nucleotide sequences. Further, the present invention provides a method and/or system of mapping ditag nucleotide sequence(s) to the genome.

According to a first aspect, the present invention provides a method of processing ditag nucleotide sequence(s), the ditag sequence comprising the 5' terminal tag and the 3' terminal tag of a nucleic acid molecule or fragment thereof or a genomic fragment, the method comprising preparing a database or file comprising at least one ditag sequence.

According to a particular aspect, the database or file of ditag sequence(s) is prepared by extracting the ditag sequence(s) from the sequences of at least one library comprising ditag(s).

The library may be a library of nucleic acid sequences, comprising at least one ditag sequence. The library may comprise at least one concatemer of ditag(s). In particular, the concatemer comprises one or more ditags. More in particular, each ditag sequence of the library of ditag(s) is flanked by a spacer nucleotide sequence and the ditag sequence(s) is extracted from the library by inputting the spacer nucleotide sequence(s). When the library of ditag(s) comprises at least a concatemer of two or more ditags, the concatemer comprises, in a 5'-3' orientation, a spacer flanking upstream the first ditag, a spacer flanking downstream the last ditag, and wherein each two neighbouring ditags are separated by a spacer positioned between them. An example of concatemer of ditags flanked and separated by spacer sequences is shown in FIG. 19. The library of ditag(s) may comprise one or more spacer sequences, each spacer sequence having a different nucleotide sequence from the other(s). The sequence size (in base pairs) of the spacers and their nucleotide sequence may depend on the restriction enzyme used in the preparation of the library. It may also depend on the experimental conditions used. Further, different spacer sequences may be used in the construction of different libraries, different tissues, different species, different concatemers, and the like.

The library may comprise ditag sequences of any kind of nucleic acid, for example, single and/or double strands of DNA and/or RNA. The ditag(s) may have been prepared from transcripts of a gene or of an exon, or they may have been prepared from portions (or locations) of the genome. Preferably, the ditags are prepared from 5' tag and 3' tag of full length cDNAs. The nucleic acid sequences of the library, comprising the ditags, are sequenced. These sequences of one or more libraries of ditag(s) may be used as a source of sequences used for the extraction of ditag sequences and for the preparation of a database or file of ditags.

More in particular, the method according to the invention comprises:
providing nucleotide sequences of a library of ditags, wherein each ditag sequence of the library of ditag(s) is flanked by a spacer nucleotide sequence, and
preparing a database or file of ditag(s) by extracting the ditag sequence(s) by inputting the spacer nucleotide sequence(s).

More in particular, the ditag sequence(s) is extracted by inputting the following parameters:
at least one spacer nucleotide sequence;
a minimal ditag base pair (bp) digit, wherein the digit is a number chosen from the range of 32-38; and
a maximal ditag base pair (bp) digit, wherein the digit is a number chosen from the range of 36-42.

Preferably, the minimal ditag base pair digit is 34 and/or the maximal ditag base pair digit is 40.

In particular, the ditag sequence(s) according to the invention may comprise a 5' terminal tag of at least 16 base pairs and a 3' terminal tag of at least 14 base pairs. Further, the ditag sequence may comprise the 5' terminal tag and the 3' terminal tag of a transcript of a gene, exon, a portion of the genome, or a fragment thereof. More in particular, the ditag sequence may comprise the 5' terminal tag and the 3' terminal tag of a full-length cDNA.

According to another aspect, the method according to the invention further comprises carrying out a quality control check of the ditag sequences of the database or file. The quality control check may be carried out at the level of library, plate, well, sequence and/or ditag. The quality control check may be carried out before mapping the ditag sequences to the genome. In view of the control check, the operator may decide eliminating from consideration sequences which result in an error and do not correspond to ditag sequences.

The step comprising mapping the ditag(s) to the genome may be carried out according to any known mapping method. In particular, the method according to the invention further comprises identifying at least one segment along the genome sequence between the matched at least one 5' terminal and the at least one 3' terminal; and identifying at least one chromosomal location, one gene, a fragment thereof, or an exon location.

According to another aspect, the method according to the present invention further comprises a step of mapping ditag(s) to the genome. In particular, the mapping step comprises mapping the at least one ditag sequence to the genome, comprising matching the 5' and the 3' terminal tags of the ditag sequence to at least a portion of the genome.

More in particular, the present invention provides a method for mapping ditag nucleotide sequence(s) to the genome, the method comprising:
preparing a database or file comprising at least one ditag sequence, the ditag sequence comprising the 5' terminal tag and the 3' terminal tag of a nucleic acid molecule or fragment thereof;
optionally carrying out a quality control check of the ditag sequences of the database or file; and
mapping the at least one ditag sequence to the genome, comprising matching the 5' and the 3' terminal tags of the ditag sequence to at least a portion of the genome.

In particular, each ditag sequence of the library of ditag(s) is flanked by a spacer nucleotide sequence and the ditag sequence(s) is extracted from the library by inputting the spacer nucleotide sequence(s).

Accordingly, the invention provides a method of mapping ditag(s) to the genome, wherein during the step of database and/or file preparation, the ditag sequence(s) is extracted by inputting the following parameters:
at least one spacer nucleotide sequence;
a minimal ditag base pair (bp) digit, wherein the digit is a number chosen from the range of 32-38;
a maximal ditag base pair (bp) digit, wherein the digit is a number chosen from the range of 36-42.

Preferably, the minimal ditag base pair digit is 34 and/or the maximal ditag base pair digit is 40.

The mapping step may further comprise identifying at least one segment along the genome sequence between the matched at least one 5' terminal and the at least one 3' terminal; and identifying at least one chromosome location, gene, exon location, or a fragment thereof. The identified gene location may result in a discovery of a new gene location.

Accordingly, the present invention also provides a method for discovering new gene(s), comprising:
preparing a database comprising at least one ditag sequence;
mapping the at least one ditag sequence to the genome, comprising matching the 5' and the 3' terminal tags of the ditag sequence to at least a portion of the genome; and
comparing the found location or sequence with existing database or data to determine whether it amounts to a new location and/or new gene.

In particular, in the method according to any aspect of the invention, the ditag sequence(s) comprises a 5' terminal tag of at least 16 base pairs (bp) and a 3' terminal tag of at least 14 base pairs (bp). In particular, 16-18 bp. Preferably, a 5' terminal tag of 18 bp and a 3' terminal tag of 16 bp.

In the method according to any aspect of the invention, the extraction of ditag sequence(s) and/or the genome mapping may be carried out through the Internet, on a computer, for example a stand-alone computer, and/or of a medium support.

According to another aspect, the present invention provides a system for processing ditag sequences. According to another aspect, the invention also provides a system of genome mapping of ditag sequences (a ditag-to-genome mapping system).

According to a particular aspect, the system according to any aspect of the invention is also referred to as GISditagTool.

Accordingly, the invention provides a system for processing ditag nucleotide sequence(s), comprising at least a module for preparing a database or file comprising at least one ditag sequence, the ditag sequence comprising the 5' terminal tag and the 3' terminal tag of a nucleic acid molecule or fragment thereof or genomic fragment.

In particular, the database or file of ditag sequence(s) is prepared by extracting the ditag sequence(s) from the sequences of at least one library comprising ditag(s).

In particular, each ditag sequence of the library of ditag(s) is flanked by a spacer nucleotide sequence and the ditag sequence(s) is extracted from the library by inputting the spacer nucleotide sequence(s). When the library of ditag(s) comprises at least a concatemer of two or more ditags, the concatemer comprises, in a 5'-3' orientation, a spacer flaking upstream the first ditag, a spacer flanking downstream the last ditag, and each two neighbouring ditags are separated by a spacer positioned between them, as described above and in particular, as shown in FIG. 19.

In particular, in the system according to invention, an operator selects at least a link, which activates the module, the module launching at least a user interface, and wherein the operator inputs into the user interface the following parameters:

at least one spacer nucleotide sequence;
a minimal ditag base pair (bp) digit, wherein the digit is a number chosen from the range of 32-38; and
a maximal ditag base pair (bp) digit, wherein the digit is a number chosen from the range of 36-42; and thereby creating a database or file of extracted ditag(s).

Preferably, the minimal ditag base pair digit is 34 and/or the maximal ditag base pair digit is 40. The user interface may be a graphical user interface.

In particular, in the system of the invention, the ditag sequence comprises the 5' terminal tag and the 3' terminal tag of a transcript of a gene, exon, a portion of the genome, or fragment thereof.

According to another aspect, the system according to the invention further comprises a module of quality control of the database or file of ditag sequences. The module for quality control may be used at the level of library, plate, well, sequence and/or ditag. The quality control check may be carried out before mapping the ditag sequences to the genome. In view of the control check, the operator may decide eliminating from consideration the sequences which result in an error and do not correspond to ditag sequences.

According to another aspect, the system according to the invention further comprises a module for mapping the at least one ditag sequence to the genome, comprising matching the 5' and the 3' terminal tags of the ditag(s) to at least a portion of the genome.

Accordingly, the present invention also provides a system for genome mapping of ditag sequences (a ditag-to-genome mapping system), comprising:
a module for preparing (creating) a database and/or file comprising at least one ditag sequence, the ditag sequence comprising the 5' terminal tag and the 3' terminal tag of a nucleic acid molecule or fragment thereof;
optionally, a module for quality control of the database or file of ditag sequence(s); and
a further module for mapping the at least one ditag sequence to the genome, comprising matching the 5' and the 3' terminal tags of the ditag(s) to at least a portion of the genome.

According to another aspect, the system according to the invention comprises at least the following:
a first user interface comprising at least a link for extracting (extractor) the ditag sequences and a link for mapping the ditag to a genome;
a second user interface, which is activated by an operator by selecting or clicking on the extractor, the second user interface comprising fields for inputting a minimal ditag base pair (bp) digit, a maximal ditag base pair (bp) digit, and the nucleotide sequence of at least one spacer sequence;
a third user interface for mapping the ditag sequence(s) to the genome or chromosome location; and
a fourth user interface showing the results of the mapping, wherein the ditag(s) is aligned to genome.

The system according to any aspect of the invention is operable by an operator on a computer and the operation is carried out through the Internet, on a computer and/or of a medium support.

According to another aspect, the invention provides a computer-readable medium comprising a computer program, the computer program being operative when associated with a computer, and wherein the computer program comprises the system according to any aspect of the invention.

With reference to the mapping step, as mentioned above, any known mapping method may be used. However, according to a particular embodiment, in order to accommodate the ditag data, a Suffix Array based Tag to Genome (SAT2G) algorithm may be used for mapping the ditag sequences to a genome sequence built and indexed on an advanced data structure Compressed Suffix Array (CSA).

Therefore, in accordance with one aspect of the invention, the method or system according to the invention also provides a mapping method and/or system comprising the steps of:
preparing a database comprising at least one ditag sequence, the ditag sequence comprising a 5' terminal tag and a 3' terminal tag from a nucleic acid molecule or fragment thereof, for example from the transcript of a gene;
matching the 5' terminal tag to at least a portion of a genome sequence to thereby identify at least one 5' site therefrom, each of the at least one 5' site having a sequence matching the 5' terminal tag;
matching the 3' terminal tag to at least a portion of the genome sequence to thereby identify at least one 3' site therefrom, each of the at least one 3' site having a sequence matching the 3' terminal tag;
identifying at least one occurring segment, each of the at least one occurring segment being a sequence segment along the genome sequence between one of the at least one 5' site and one of the at least one 3' site, each of the at least one occurring segment having a sequence length; and
identifying at least one feasible gene location, each of the feasible gene location being one of the at least one occurring segment having a sequence length not exceeding that of a predefined gene length.

According to another aspect of the invention, it is provided a mapping system comprising:
means for preparing a database by extracting at least one ditag, the ditag comprising a 5' terminal tag and a 3' terminal tag from a nucleic acid molecule or fragment thereof, for example from a transcript of a gene;
means for matching the 5' terminal tag to at least a portion of a genome sequence to thereby identify at least one 5' site therefrom, each of the at least one 5' site having a sequence matching the 5' terminal tag;
means for matching the 3' terminal tag to at least a portion of the genome sequence to thereby identify at least one 3' site therefrom, each of the at least one 3' site having a sequence matching the 3' terminal tag;
means for identifying at least one occurring segment, each of the at least one occurring segment being a sequence segment along the genome sequence between one of the at least one 5' site and one of the at least one 3' site, each of the at least one occurring segment having a sequence length; and
means for identifying at least one feasible gene location, each of the feasible gene location being one of the at least one occurring segment having a sequence length not exceeding that of a predefined gene length.

According to another aspect of the invention, it is provided a mapping method comprising the steps of:
preparing a ditag database comprising extracting at least one ditag, for example from a library of ditags or from existing database(s) of ditags, the ditag comprising a 5' terminal tag and a 3' terminal tag from a nucleic acid molecule of fragment thereof, for example a transcript of a gene;
matching the 5' terminal tag to at least a portion of a genome sequence to thereby identify at least one 5' site therefrom, each of the at least one 5' site having a sequence matching the 5' terminal tag;

matching the 3' terminal tag to at least a portion of the genome sequence to thereby identify at least one 3' site therefrom, each of the at least one 3' site having a sequence matching the 3' terminal tag;

identifying at least one occurring segment, each of the at least one occurring segment being a sequence segment along the genome sequence between one of the at least one 5' site and one of the at least one 3' site, each of the at least one occurring segment having a sequence length; and identifying at least one feasible gene location from the at least one occurring segment, each of the at least one feasible gene location being one of the at least one occurring segment with at least one of the sequence length thereof not exceeding that of the predefined gene length, the sequence order thereof and of the at least one 5' site and one of the at least one 3' site corresponding thereto in accordance with a 5'-occurring segment-3' structure matching the sequence order of the corresponding portion of the genome sequence, the 5' site and one of the at least one 5' site and one of the at least one 3' site corresponding thereto having a 5'-3' orientation, and one of the at least one 5' site and one of the at least one 3' site corresponding to each of the occurring segment being located within the same chromosome.

BRIEF DESCRIPTION OF THE FIGURES

FIG. 6 shows a pseudo code "Find_Sites" of the transcript mapping method of FIG. 3 for forward and reverse searching of 5' sites and 3' sites from a genome sequence.

FIG. 7 shows a pseudo code "Match_sites_1" of the transcript mapping method of FIG. 3 for identifying the sequence length of an occurring segment, the sequence length being subsequently compared with a predefined length for identifying of a feasible gene location therefrom.

FIG. 8 shows a pseudo code "Match_sites_2" of the transcript mapping method of FIG. 3 for identifying an occurring segment when a disparity condition is met wherefrom a feasible gene location is subsequently obtained.

FIG. 11 shows a Project Module flow chart, FIG. 12 shows an Extractor Module flow chart, FIG. 13 shows an Examiner Module flow chart, and FIG. 14 shows a Mapping Module flow chart.

FIG. 15. Extraction and quality control (QC) user interfaces (from A to F) of GISditagTool. Sequence reads can be uploaded for ditag extraction via the extractor module (B). The extraction parameters can be modified at this stage. QC is conducted in sequential order. The very top panel (A) shows the statistics of all the projects. When the Examiner module is activated, ditag statistics for all the libraries is shown (C). Clicking on a library, a plate in a library, and then a well in a plate, the user is able to evaluate the quality of plates (D), wells (E), and sequence (F), respectively.

FIG. 16 shows the user interfaces (A) and (B) of GISditagTool of FIG. 15.

FIG. 17 shows the user interfaces (C) and (D) of GISditagTool of FIG. 15.

FIG. 19 shows the user interface (F) of GISditagTool of FIG. 15.

DEFINITIONS

Figure 1:
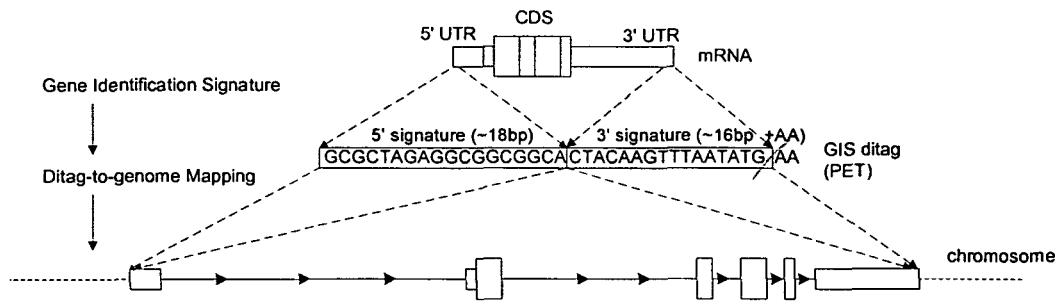
FIG. 1. The structure of GIS ditag and GIS ditag-to-genome mapping. In the example shown in this figure, GIS ditags are generated from full-length cDNA library. Each ditag [SEQ ID NO: 1] comprises a 5' and a 3' tags (~18 bp each) corresponding to the termini of the full-length clone. Direct GIS ditag-to-genome mapping of the ditag locates the boundaries of the corresponding gene in the chromosome.

Ditag: GISditag(s), also referred to as ditag(s), is defined and prepared according to US 2005/0059022, the whole content of which is herein incorporated by reference.

Data: Information, in any form, on which a computer program operates. Data, as herein used, encompasses any information regarding ditags, in particular, to base pairs of ditag(s) and the nucleotide sequence of ditag(s).

Data Management system: also referred to as DBMS or dbms, is a software system that provides comprehensive facilities for the organization and management of a body of data required for a particular application or group of related applications.

Database: for the purposes of the present invention, a collection of data (or in general information) of ditag(s) comprising at least the nucleotide sequence of ditag(s) in a DBMS. It may also comprise further information such as the size in base pairs (bp) and the nucleotide sequence of one or more spacer used, orientation of ditag(s), a library or sequence identification (ID) number, and the like. The data or information are collected, accessed and/or stored within a computer system and/or a computer-readable medium. The database may also be available on the Internet. The definition of database also includes a body of information or data held within a computer system and/or a computer-readable medium using the facilities of a database management system.

File (also referred to as computer file): A collection of information, referred to by file name; for example, a user-created document, program data, or the program itself. For the purposes of the present invention, it is defined as a collection of data (or in general information) of ditag(s) comprising at least the nucleotide sequence of ditag(s). It may also comprise further information such as the size in base pairs (bp) and the nucleotide sequence of one or more spacer used, orientation of ditag(s), a library or sequence identification (ID) number, count (copy number) and the like. The data or information are collected, accessed and/or stored within a computer system and/or a computer-readable medium. The file may also be available on the Internet. One or more files of ditag(s) may be collected in a directory of files.

DETAILED DESCRIPTION OF THE INVENTION

Complete genome annotation relies on precise identification of transcription units bounded by a transcription initiation site (TIS) and a polyadenylation site (PAS). To facilitate this, a pair of complementary methods, namely 5'LongSAGE (long serial analysis of gene expression) and 3'LongSAGE, was developed (Wei et al., 2004, see above). These methods are based on the original SAGE (serial analysis of gene expression) and LongSAGE methods that utilize typical full-length cDNA cloning technologies to enable high-throughput extraction of the first and the last 20 base pairs (bp) of each transcript. Mapping of 5' and 3' LongSAGE tags to the genome allows the localization of the TIS and the PAS.

However, matching of 5' and 3' tags derived from same transcripts in genome sequences are not always straightforward and can sometimes be very ambiguous. One solution is to clone the 5' and 3' tags of the same transcript by interlinking the 5' and 3' tags. To achieve this, a specially designed device comprising cloning adapters and a vector link the 5' tag and the 3' tag derived from the same transcript into a ditag.

A plurality of ditags can be concatenated for cloning and sequencing, with each ditag representing an individual transcript. Unlike single tag sequences, the paired ditag sequences can be specifically multiplied with a frame of transcripts being precisely definable when being mapped to the genome sequences. This approach, named Gene Identification Signature (GIS) analysis, which can accurately map the 5' and 3' ends of transcription units encoded by genes or of nucleic acid molecule or fragments thereof, is described in the US patent application published with the number US 2005/0059022 (the whole content of which is herein incorporated by reference).

Figure 2:
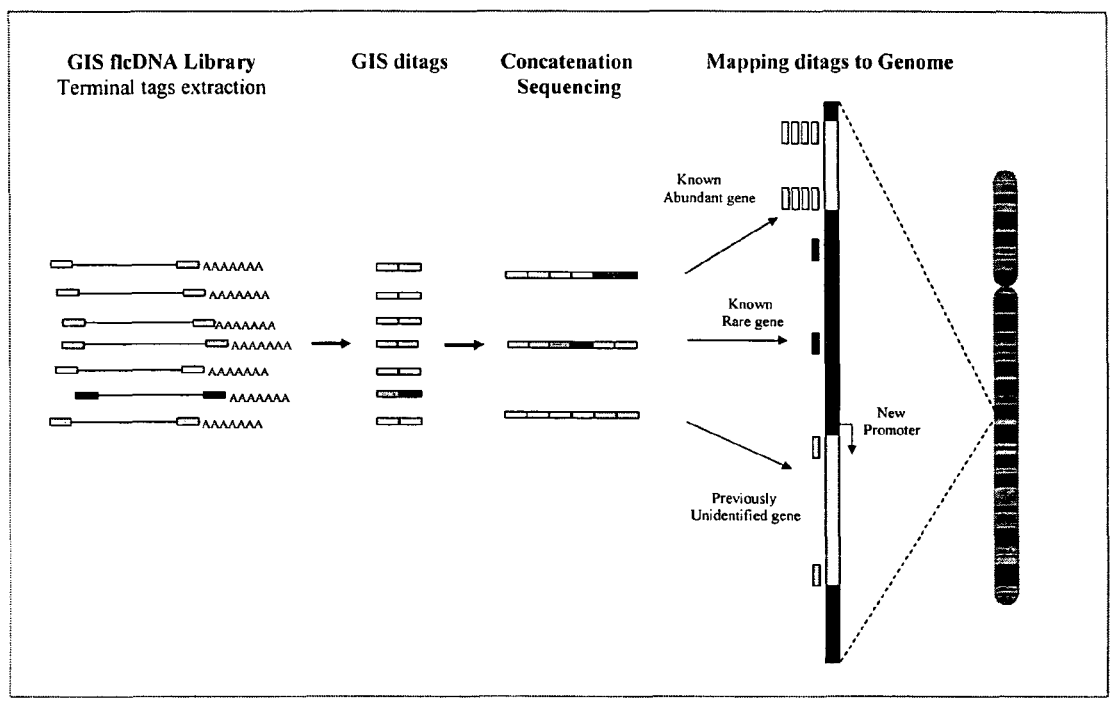
FIG. 2 shows a schematic diagram of a 5' and 3' terminal tags of GIS ditag (herein also referred to as ditag) technique for use in genome annotation. This figure also shows the preparation of concatemers of ditags.

An example of the GIS analysis (also indicated as GIS technology or methodology) is shown in FIGS. 1 and 2. According to a particular aspect of the GIS analysis, the conventional cap-trapper method is applied to enrich a full-length cDNA and incorporated adapter sequences that bear a MmeI restriction site at each end of the cDNA fragments. The cDNA fragments are then cloned in a cloning vector to construct a GIS flcDNA (full-length cDNA) library. However, the GIS methodology is not limited to flcDNA, but may be applied to any nucleic acid molecule or fragment thereof, for example to a portion of a genome. The plasmid prepared from the library is digested by MmeI (a type II restriction enzyme) and cleaved 20 bp downstream of its binding site. However, any restriction enzyme recognizing an asymmetric restriction site may be used in the GIS methodology. In particular, any type II restriction enzyme suitable for the purpose of the GIS methodology may be used. After digestion, the flcDNA inserts of the library were dropped from the plasmid to leave 18 bp signatures of 5' and 3' ends with the learned cloning vector. Re-circling the vector would create a GIS single ditag library. The ditags of the library were then sliced out and purified for concatenating and cloning to generate the final GIS ditag library for sequence analysis. Typically, each sequence read of the GIS ditag clones reveals 15 ditags. Each unit of the ditag sequence contains 5' tag signature of at least 16 base pairs (bp) and 3' tag signature of at least 14 bp, with a spacer to separate one ditag sequence from another. In particular, the ditag comprises 18 bp of 5' and 18 bp of 3' signatures. More in particular, the ditag comprises 18 bp of 5' and 16 bp of 3' signatures. The length of the spacer sequence depends on the enzyme used or on the experimental conditions used, for example the spacer may be 12 bp.

Libraries comprising GISditags (also simply indicated as ditags) may therefore be prepared as mentioned above. The sequences of the nucleic acid molecules of the library comprising the ditags are then sequenced. The sequence information may be collected in one or more databases. However, at present, no efficient methods for the selection of ditag sequences from these libraries, as well as the construction of ditag databases have been disclosed.

Further, the ditags require to be mapped to find their corresponding genes on the genome. However, no mapping methods have been specifically disclosed for ditags. Further, there are no existing computer algorithms that are readily applicable for mapping the ditag sequences to the genome.

Accordingly, the present invention provides a new method and/or system of processing ditag sequence(s). Further, the present invention provides a method and/or system for mapping ditag nucleotide sequence(s) to the genome. According to a particular aspect, the method and system according to the invention will be explained with particular reference, but is not limited to, a method and system indicated as the GISditagTool. In particular, the GISditagTool will be explained in more detail with reference to FIGS. 10 to 20.

According to a first aspect, the present invention provides a method of processing ditag nucleotide sequence(s), the ditag sequence comprising the 5' terminal tag and the 3' terminal tag of a nucleic acid molecule or fragment thereof or a genomic fragment, the method comprising preparing a database or file comprising at least one ditag sequence.

According to a particular aspect, the database or file of ditag sequence(s) is prepared by extracting the ditag sequence(s) from the sequences of at least one library comprising ditag(s).

The library may be a library of nucleic acid sequences, comprising at least one ditag sequence. The library may comprise at least one concatemer of ditag(s). In particular, the concatemer comprises one or more ditags. More in particular, each ditag sequence of the library of ditag(s) is flanked by a spacer nucleotide sequence and the ditag sequence(s) is extracted from the library by inputting the spacer nucleotide sequence(s). When the library of ditag(s) comprises at least a concatemer of two or more ditags, the concatemer comprises, in a 5'-3' orientation, a spacer flanking upstream the first ditag, a spacer flanking downstream the last ditag, and each two neighbouring ditags are separated by a spacer positioned between them. An example of concatemer of ditags flanked and separated by spacer sequences is shown in FIG. 19. The 5' flanking spacer and/or the 3' flanking spacer may vary in length. In particular, their length may vary among a concatemer of ditags or within the concatamers of ditags of one or more libraries. The library of ditag(s) may comprise one or more spacer sequences, each spacer sequence having different nucleotide sequence from the other(s). The spacers sequence size (in base pairs) and the respective nucleotide sequence may depend on the restriction enzyme used in the preparation of the library. It may also depend on the experimental conditions used. Further, different spacer sequences may be used in the construction of different libraries, different tissues, different species, different concatemers, and the like.

In FIG. 19, there is provided an example of arrangement of ditags and spacers in a concatemer of ditags. In particular, FIG. 19 shows ditags flanked and separated by spacers. In particular, the spacers used showed in FIG. 19 all have the same nucleotide sequence and a size of 12 bp. However, spacers having different nucleotide sequence from each other may also be used. In a 5'-3' orientation, FIG. 19 shows a portion of the vector (58 bp) flanking the first spacer. The first spacer flanks upstream the first ditag (38 bp). The first ditag (38 bp) and the second ditag (37 bp) are separated by the spacer. The same situation is up to the right ditag. The eighth ditag (36 bp) is then followed (flanked) downstream by the last spacer, which is flanked downstream by a portion of the vector (52 bp). It will be evident to a skilled person that the concatemer may comprise a variable number of ditags and it is not limited to eight ditags as shown as example in FIG. 19. Further, one or more spacers having a different nucleotide sequence from the other may also be used. The size of the spacer may also be variable, as explained above.

The library may comprise ditag sequences of any kind of nucleic acid, for example, single and/or double strands of DNA and/or RNA. The ditag(s) may have been prepared from transcripts of a gene or of an exon, or they may have been prepared from portions (or locations) of the genome. Preferably, the ditags are prepared from 5' tag and 3' tag of full length cDNAs. The nucleic acid sequences of the library, comprising the ditags, are sequenced. These sequences of one or more libraries of ditag(s) may be used as a source for the extraction of ditag sequences and for the preparation of database or file of ditags.

More in particular, the method according to the invention comprises:
  providing nucleotide sequences of a library of ditags, wherein each ditag sequence of the library of ditag(s) is flanked by a spacer nucleotide sequence, and
  preparing a database or file of ditag(s) by extracting the ditag sequence(s) by inputting the spacer nucleotide sequence(s).

More in particular, the ditag sequence(s) is extracted by inputting the following parameters:
  at least one spacer nucleotide sequence;
  a minimal ditag base pair (bp) digit, wherein the digit is a number chosen from the range of 32-38; and
  a maximal ditag base pair (bp) digit, wherein the digit is a number chosen from the range of 36-42.

Preferably, the minimal ditag base pair digit is 34 and/or the maximal ditag base pair digit is 40.

In particular, the ditag sequence(s) according to the invention may comprise a 5' terminal tag of at least 16 base pairs and a 3' terminal tag of at least 14 base pairs. Further, the ditag sequence may comprise the 5' terminal tag and the 3' terminal tag of a transcript of a gene, exon, a portion of the genome, or fragment thereof. More in particular, the ditag sequence may comprise the 5' terminal tag and the 3' terminal tag of a full-length cDNA.

According to another aspect, the method according to the invention further comprises carrying out a quality control check of the ditag sequences of the database or file. The quality control check may be carried out at the level of library, plate, well, sequence and/or ditag. The quality control check may be carried out before mapping the ditag sequences to the genome. In view of the control check, the operator may decide eliminating from consideration the sequences which result in an error and do not correspond to ditag sequences.

The step comprising mapping the ditag(s) to the genome may be carried out according to any known mapping method. In particular, the method according to the invention further comprises identifying at least one segment along the genome sequence between the matched at least one 5' terminal and the at least one 3' terminal; and identifying at least one chromosomal location, one gene, a fragment thereof, or an exon location.

According to a particular aspect, the present invention provides a mapping step referred to as SAT2G (suffix array-based tag-to-genome), which will be described in more detail below.

According to another aspect, the method according to the present invention further comprises a step of mapping ditag(s) to the genome. In particular, the mapping step comprises mapping the at least one ditag sequence to the genome, comprising matching the 5' and the 3' terminal tags of the ditag sequence to at least a portion of the genome.

More in particular, the present invention provides a method for mapping ditag nucleotide sequence(s) to the genome, the method comprising:
  preparing a database or file comprising at least one ditag sequence, the ditag sequence comprising the 5' terminal tag and the 3' terminal tag of a nucleic acid molecule or fragment thereof;
  optionally carrying out a quality control check of the ditag sequences of the database or file; and
  mapping the at least one ditag sequence to the genome, comprising matching the 5' and the 3' terminal tags of the ditag sequence to at least a portion of the genome.

In particular, each ditag sequence of the library of ditag(s) is flanked by a spacer nucleotide sequence and the ditag sequence(s) is extracted from the library by inputting the spacer nucleotide sequence(s).

Accordingly, the invention provides a method of mapping ditag(s) to the genome, wherein during the step of database and/or file preparation, the ditag sequence(s) is extracted by inputting the following parameters:
  at least one spacer nucleotide sequence;
  a minimal ditag base pair (bp) digit, wherein the digit is a number chosen from the range of 32-38;
  a maximal ditag base pair (bp) digit, wherein the digit is a number chosen from the range of 36-42.

Preferably, the minimal ditag base pair digit is 34 and/or the maximal ditag base pair digit is 40.

The mapping step may further comprise identifying at least one segment along the genome sequence between the matched at least one 5' terminal and the at least one 3' terminal; and identifying at least one chromosome location, gene, exon location, or a fragment thereof. The identified gene location may result in the discovery of a new gene location.

Accordingly, the present invention also provides a method for discovering new gene(s), comprising:
  preparing a database comprising at least one ditag sequence;

mapping the at least one ditag sequence to the genome, comprising matching the 5' and the 3' terminal tags of the ditag sequence to at least a portion of the genome; and comparing the found location or sequence with existing database or data to determine whether it amounts to a new location and/or new gene.

In particular, in the method according to any aspect of the invention, the ditag sequence(s) comprises a 5' terminal tag of at least 16 base pairs (bp) and a 3' terminal tag of at least 14 base pairs (bp). In particular, 16-18 bp. Preferably, a 5' terminal tag of 18 bp and a 3' terminal tag of 16 bp.

In the method according to any aspect of the invention, the extraction of ditag sequence(s) and/or the genome mapping may be carried out through the Internet, on a computer, for example a stand-alone computer, and/or of a medium support.

According to another aspect, the present invention provides a system for processing ditag sequences. According to another aspect, the invention also provides a system of genome mapping of ditag sequences (a ditag-to-genome system). According to a particular aspect, the system according to any aspect of the invention is also referred to as GISditagTool. More in particular, the GISditagtool is a software program system. The GISditagTool may be provided on a medium support, installed on a hard drive disk, or made available through the Internet. Accordingly, the invention also provides a GISditagTool software program package (kit).

Accordingly, the invention provides a system for processing ditag nucleotide sequence(s), comprising at least a module for preparing a database or a file comprising at least one ditag sequence, the ditag sequence comprising the 5' terminal tag and the 3' terminal tag of a nucleic acid molecule or fragment thereof or genomic fragment.

In particular, the database or file of ditag sequence(s) is prepared by extracting the ditag sequence(s) from the sequences of at least one library comprising ditag(s).

In particular, each ditag sequence of the library of ditag(s) is flanked by a spacer nucleotide sequence and the ditag sequence(s) is extracted from the library by inputting the spacer nucleotide sequence(s). When the library of ditag(s) comprises at least a concatemer of two or more ditags, the concatemer comprises, in a 5'-3' orientation, a spacer flaking upstream the first ditag, a spacer flanking downstream the last ditag, and each two neighbouring ditags are separated by a spacer positioned between them, as described above and in particular, as shown in FIG. 19.

In particular, in the system according to invention, an operator selects at least a link, which activates the module, the module launching at least a user interface, and wherein the operator inputs into the user interface the following parameters:

at least one spacer nucleotide sequence;
a minimal ditag base pair (bp) digit, wherein the digit is a number chosen from the range of 32-38; and
a maximal ditag base pair (bp) digit, wherein the digit is a number chosen from the range of 36-42; and
thereby creating a database or file of extracted ditag(s).

Preferably, the minimal ditag base pair digit is 34 and/or the maximal ditag base pair digit is 40. The user interface may be a graphical user interface.

In particular, in the system of the invention, the ditag sequence comprises the 5' terminal tag and the 3' terminal tag of a transcript of a gene, exon, a portion of the genome, or fragment thereof.

According to another aspect, the system according to the invention further comprises a module for quality control of the database or file of ditag sequences. The module for quality control may be used at the level of library, plate, well, sequence and/or ditag. The quality control check may be carried out before mapping the ditag sequences to the genome. In view of the control check, the operator may decide eliminating from consideration the sequences which result in an error and do not correspond to ditag sequences.

According to another aspect, the system according to the invention further comprises a module for mapping the at least one ditag sequence to the genome, comprising matching the 5' and the 3' terminal tags of the ditag(s) to at least a portion of the genome.

Accordingly, the present invention also provides a system for genome mapping of ditag sequences (a ditag-to-genome mapping system), comprising:

a module for preparing (creating) a database and/or file comprising at least one ditag sequence, the ditag sequence comprising the 5' terminal tag and the 3' terminal tag of a nucleic acid molecule or fragment thereof;

optionally, a module for quality control of the database or file of ditag sequence(s); and a further module for mapping the at least one ditag sequence to the genome, comprising matching the 5' and the 3' terminal tags of the ditag(s) to at least a portion of the genome.

According to another aspect, the system according to the invention comprises at least the following:

a first user interface comprising at least a link for extracting (extractor) the ditag sequences and a link for mapping the ditag to a genome;

a second user interface, which is activated by an operator by selecting or clicking on the extractor, the second user interface comprising fields for inputting a minimal ditag base pair (bp) digit, a maximal ditag base pair (bp) digit, and the nucleotide sequence of at least one spacer sequence;

a third user interface for mapping the ditag sequence(s) to the genome or chromosome location; and a fourth user interface showing the results of the mapping, wherein the ditag(s) is aligned to genome.

The system according to any aspect of the invention is operable by an operator on a computer and the operation is carried out through the Internet, on a computer and/or of a medium support.

According to another aspect, the invention provides a computer-readable medium comprising a computer program, the computer program being operative when associated with a computer, and wherein the computer program comprises the system according to any aspect of the invention.

Mapping Step

Mapping ditags to the genome is akin to searching occurrences of a pattern in the genome sequence. Approaches for pattern searching include the conventional BLAST (basic local alignment search tool) and BLAT (BLAST-like alignment tool) method. Both the BLAST and BLAT methods are slow because each thereof requires a pattern to be searched by scanning through the whole genome. Moreover, conventional full-text indexing is usually employed if exact occurrences of a pattern with a small mismatch margin are required. Efficient full-text indexing data-structures include a suffix tree and a suffix array.

Figure 5:
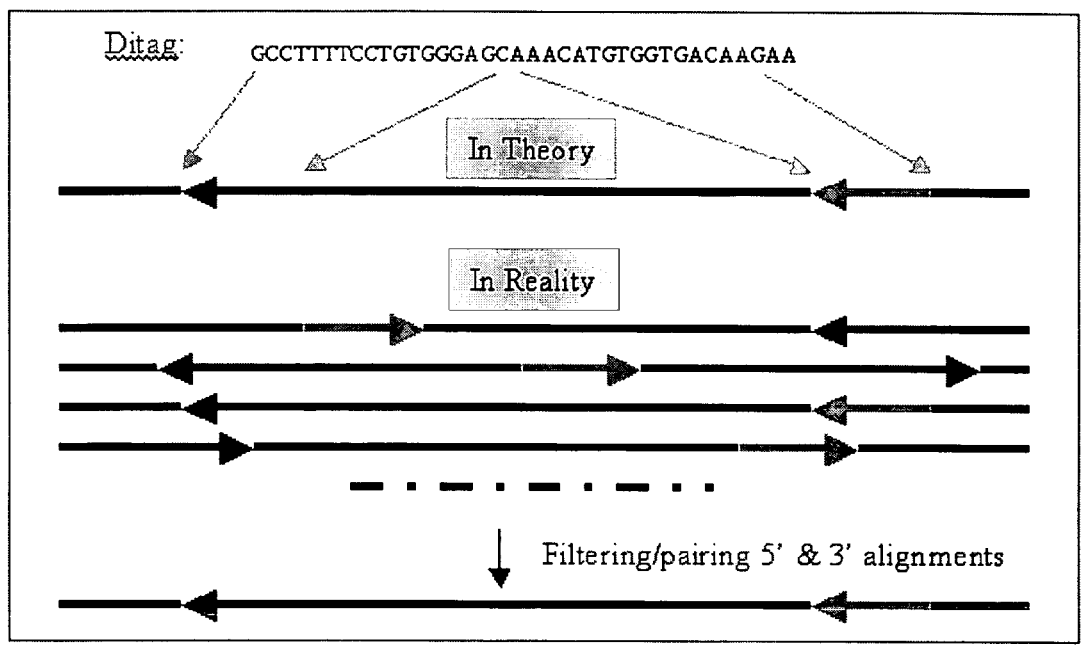
FIG. 5 shows GIS ditag [SEQ ID NO: 2] (PET)-to-genome mapping. Mapping PET sequences with SAT2G is conducted in two steps. First, the 5' tags and 3' tags are aligned independently against a genome assembly; a 16 bp perfect match length is required for 5' tag and 14 bp required for the 3' tag. Then, in the second step, the 5'alignments are paired with the corresponding 3' alignments in search of the target location(s) in the chromosomes. A target is identified if both of the 5' and 3' tags are in the same chromosome, same strand, same orientation, in 5' followed by 3' order, and within 1 million by distance.

As mentioned above, any known mapping method may be used. However, according to a particular embodiment, in order to accommodate the ditag data, a Suffix Array based Tag to Genome (SAT2G) algorithm may be used for mapping the ditag sequences to a genome sequence built and indexed on an advanced data structure Compressed Suffix Array (CSA). A schematic example of GIS ditag (PET)-to-genome mapping using SAT2G is shown in FIG. 5. The SAT2G system is disclosed in more details in FIGS. 6 to 8.

Therefore, in accordance with one aspect of the invention, the method or system according to the invention also provides a mapping method or system comprising the steps of:

preparing a database comprising at least one ditag sequence, the ditag sequence comprising a 5' terminal tag and a 3' terminal tag from a nucleic acid molecule or fragment thereof, for example from a transcript of a gene;

matching the 5' terminal tag to at least a portion of a genome sequence to thereby identify at least one 5' site therefrom, each of the at least one 5' site having a sequence matching the 5' terminal tag;

matching the 3' terminal tag to at least a portion of the genome sequence to thereby identify at least one 3' site therefrom, each of the at least one 3' site having a sequence matching the 3' terminal tag;

identifying at least one occurring segment, each of the at least one occurring segment being a sequence segment along the genome sequence between one of the at least one 5' site and one of the at least one 3' site, each of the at least one occurring segment having a sequence length; and identifying at least one feasible gene location, each of the feasible gene location being one of the at least one occurring segment having a sequence length not exceeding that of a predefined gene length.

In the nucleic acid (for example a transcript) mapping method, the step of matching the 5' terminal tag to at least a portion of a genome sequence may comprise the step of:

matching the 5' terminal tag to a chromosome sequence.

In the mapping method, the step of matching the 3' terminal tag to at least a portion of the genome sequence may comprise the step of:

matching the 3' terminal tag to a chromosome sequence.

The transcript mapping method may further comprise the step of generating a data structure for indexing the genome sequence.

The mapping method may further comprise the step of generating at least one of a tree structure and an ordered array for indexing the genome sequence.

The mapping method may further comprise the step of generating at least one of a suffix array, a suffix tree, a binary tree and a compressed suffix array for indexing the genome sequence.

In the mapping method, the step of matching the 5' terminal tag to at least a portion of a genome sequence may comprise the step of:

at least one of forward traversing and reverse traversing the genome sequence for comparing the 5' terminal tag to at least a portion of the genome sequence to obtain the at least one 5' site.

In the transcript mapping method, the step of the matching the 3' terminal tag to at least a portion of a genome sequence may comprise the step of:

at least one of forward traversing and reverse traversing the genome sequence for comparing the 3' terminal tag to at least a portion of the genome sequence to obtain the at least one 3' site.

In the transcript mapping method, the step of identifying at least one feasible gene location may comprise the step of comparing sequence order of each of the at least one occurring segment and one of the at least one 5' site and one of the at least one 3' site corresponding thereto to at least a portion of the genome sequence for obtaining the at least one feasible gene location therefrom.

In the transcript mapping method, the step of comparing sequence order of each of the at least one occurring segment and one of the at least one 5' site and one of the at least one 3' site corresponding thereto may comprise the step of comparing the sequence order of each of the at least one occurring segment and one of the at least one 5' site and one of the at least one 3' site corresponding thereto being in accordance with a 5'-occurring segment-3' structure.

In the transcript mapping method, the step of identifying at least one feasible gene location may comprise the step of identifying the 5'-3' orientation of each of the at least one occurring segment for obtaining the at least one feasible gene location therefrom.

In the transcript mapping method, the step of identifying the 5'-3' orientation may comprise the step of identifying a residual AA nucleotide, the residual AA neucleotide constituting a portion of the 3' terminal tag.

In the transcript mapping method, the step of identifying at least one feasible gene location may comprise the step of:

identifying the chromosome wherein each of one of the at least one 5' site and one of the at least one 3' site corresponding to each of the occurring segment is located for identifying the at least one feasible gene location therefrom.

In the transcript mapping method, the step of matching the 5' terminal tag to at least a portion of a genome sequence may comprise the step of:

identifying quantity of the at least one 5' site, and the step of matching the 3' terminal tag to at least a portion of a genome sequence comprising the step of:

identifying quantity of the at least one 3' site.

In the transcript mapping method, the step of identifying at least one occurring segment may comprise the step of:

traversing along the genome sequence towards one of the extremities thereof from each of the at least one 5' site for identifying at least one of the at least one 3' site.

In the transcript mapping method, the step of identifying the at least one feasible gene location may comprise the step of:

terminating traversal along the genome sequence in response to one of the at least one feasible gene location being identified for each of the at least one 5' site.

In the transcript mapping method, the step of identifying at least one occurring segment may comprise the step of:

traversing along the genome sequence towards one of the extremities thereof from each of the at least one 3' site for identifying at least one of the at least one 5' site.

In the transcript mapping method, the step of identifying the at least one feasible gene location may comprise the step of:

terminating traversal along the genome sequence in response to one of the at least one feasible gene location being identified for each of the at least one 3' site.

According to another aspect of the invention, it is provided a mapping system comprising:

means for preparing a database by extracting at least one ditag, the ditag comprising a 5' terminal tag and a 3' terminal tag from a nucleic acid molecule or fragment thereof, for example form a transcript of a gene;

means for matching the 5' terminal tag to at least a portion of a genome sequence to thereby identify at least one 5' site therefrom, each of the at least one 5' site having a sequence matching the 5' terminal tag;

means for matching the 3' terminal tag to at least a portion of the genome sequence to thereby identify at least one 3' site therefrom, each of the at least one 3' site having a sequence matching the 3' terminal tag;

means for identifying at least one occurring segment, each of the at least one occurring segment being a sequence segment along the genome sequence between one of the at least one 5' site and one of the at least one 3' site, each of the at least one occurring segment having a sequence length; and means for identifying at least one feasible gene location, each of the feasible gene location being one of the at least one occurring segment having a sequence length not exceeding that of a predefined gene length.

In the mapping system, the means for identifying a 5' terminal tag and a 3' terminal tag may comprise:

means for providing a nucleotide sequence with at least 16 base pairs for forming the 5' terminal tag; and means for providing a nucleotide sequence with at least 16 base pairs for forming the 3' terminal tag.

In the mapping system, the means for matching the 5' terminal tag to at least a portion of a genome sequence may comprise:

means for matching the 5' terminal tag to a chromosome sequence.

In the mapping system, the means for matching the 3' terminal tag to at least a portion of the genome sequence may comprise:

means for matching the 3' terminal tag to a chromosome sequence.

The mapping system may further comprise:

means for generating a data structure for indexing the genome sequence.

The mapping system may further comprise:

means for generating at least one of a tree structure and an ordered array for indexing the genome sequence.

The mapping system may further comprise:

means for generating at least one of a suffix array, a suffix tree, a binary tree and a compressed suffix array for indexing the genome sequence.

In the mapping system, the means for matching the 5' terminal tag to at least a portion of a genome sequence may comprise:

means for at least one of forward traversing and reverse traversing the genome sequence for comparing the 5' terminal tag to at least a portion of the genome sequence to obtain the at least one 5' site.

In the mapping system, the means for matching the 3' terminal tag to at least a portion of a genome sequence may comprise:

means for at least one of forward traversing and reverse traversing the genome sequence for comparing the 3' terminal tag to at least a portion of the genome sequence to obtain the at least one 3' site.

In the mapping system, the means for identifying at least one feasible gene location may comprise:

means for comparing sequence order of each of the at least one occurring segment and one of the at least one 5' site and one of the at least one 3' site corresponding thereto to at least a portion of the genome sequence for obtaining the at least one feasible gene location therefrom.

In the mapping system, the means for comparing sequence order of each of the at least one occurring segment and one of the at least one 5' site and one of the at least one 3' site corresponding thereto may comprise the means for comparing the sequence order of each of the at least one occurring segment and one of the at least one 5' site and one of the at least one 3' site corresponding thereto being in accordance with a 5'-occurring segment-3' structure.

In the mapping system, the means for identifying at least one feasible gene location may comprise:

means for identifying the 5'-3' orientation of each of the at least one occurring segment for obtaining the at least one feasible gene location therefrom.

In the mapping system, the means for identifying the 5'-3' orientation may comprise:

means for identifying a residual AA nucleotide, the residual AA nucleotide constituting a portion of the 3' terminal tag.

In the mapping system, the means for identifying at least one feasible gene location may comprise:

means for identifying the chromosome wherein each of one of the at least one 5' site and one of the at least one 3' site corresponding to each of the occurring segment is located for identifying the at least one feasible gene location therefrom.

In the mapping system, the means for matching the 5' terminal tag to at least a portion of a genome sequence may comprise:

means for identifying a quantity of the at least one 5' site, and the means for matching the 3' terminal tag to at least a portion of a genome sequence comprising:

means for identifying quantity of the at least one 3' site.

In the mapping system, the means for identifying at least one occurring segment may comprise:

means for traversing along the genome sequence towards one of the extremities thereof from each of the at least one 5' site for identifying at least one of the at least one 3' site.

In the mapping system, the means for identifying the at least one feasible gene location may comprise:

means for terminating traversal along the genome sequence in response to one of the at least one feasible gene location being identified for each of the at least one 5' site.

In the mapping system, the means for identifying at least one occurring segment may comprise:

means for traversing along the genome sequence towards one of the extremities thereof from each of the at least one 3' site for identifying at least one of the at least one 5' site.

In the mapping system, the means for identifying the at least one feasible gene location may comprise:

means for terminating traversal along the genome sequence in response to one of the at least one feasible gene location being identified for each of the at least one 3' site.

According to another aspect of the invention, it is provided a mapping method comprising the steps of:

preparing a ditag database comprising extracting at least one ditag, for example from a library of ditags or from existing database(s) of ditags, the ditag comprising a 5' terminal tag and a 3' terminal tag from a nucleic acid molcule of fragment thereof, for example a transcript of a gene;

matching the 5' terminal tag to at least a portion of a genome sequence to thereby identify at least one 5' site therefrom, each of the at least one 5' site having a sequence matching the 5' terminal tag;

matching the 3' terminal tag to at least a portion of the genome sequence to thereby identify at least one 3' site therefrom, each of the at least one 3' site having a sequence matching the 3' terminal tag;

identifying at least one occurring segment, each of the at least one occurring segment being a sequence segment along the genome sequence between one of the at least one 5' site and one of the at least one 3' site, each of the at least one occurring segment having a sequence length; and identifying at least one feasible gene location from the at least one occurring segment, each of the at least one feasible gene location being one of the at least one occurring segment with at least one of the sequence length thereof not exceeding that of the predefined gene length, the sequence order thereof and of the at least one 5' site and one of the at least one 3' site corresponding thereto in accordance with a 5'-occurring segment-3' structure matching the sequence order of the corresponding portion of the genome sequence, the 5' site and one of the at least one 5' site and one of the at least one 3' site corresponding thereto having a 5'-3' orientation, and one of the at least one 5' site and one of the at least one 3' site corresponding to each of the occurring segment being located within the same chromosome.

As mentioned above, efficient full-text indexing data-structures include a suffix tree and a suffix array. A suffix tree is a tree-like data-structure having branches stemming from a root with each branch terminating at a leaf that encodes a suffix of the genome sequence. The suffix array is a sorted sequence of all suffices of the genome according to lexicographic order. The suffix array is represented as an array SA[i] where i=1 ... n and that SA[i]=j means that the j-suffix (suffix starting from character j) is the i-th smallest suffix in the lexicographic order.

Both the suffix tree and the suffix array allow for fast pattern searching. Given a pattern of length x, its occurrences in the genome G[1 ... n] can be reported in O(x) time and O(x log n) time for the suffix tree and the suffix array respectively. Although the query time is fast, it is not always feasible to build the suffix tree or the suffix array due to large space requirements thereof. For example, for a mouse genome, the suffix tree and the suffix array require 40 Gigabytes (GB) and 13 GB respectively. Such memory requirement far exceeds the memory space capacity of ordinary computers. To solve the memory space problem, we apply the space-efficient compressed suffix array (CSA) indexing data structure. CSA is a compressed form of the suffix array. It can be built efficiently without the need for enormous memory requirements using known algorithms. Also, the built CSA is very small. For example, a CSA for the mouse genome (mm3) occupies approximately 1.3 GB. Additionally, CSA is also able to support efficient searching. Searching a pattern of length x requires only O(x log n) time.

Figure 3:
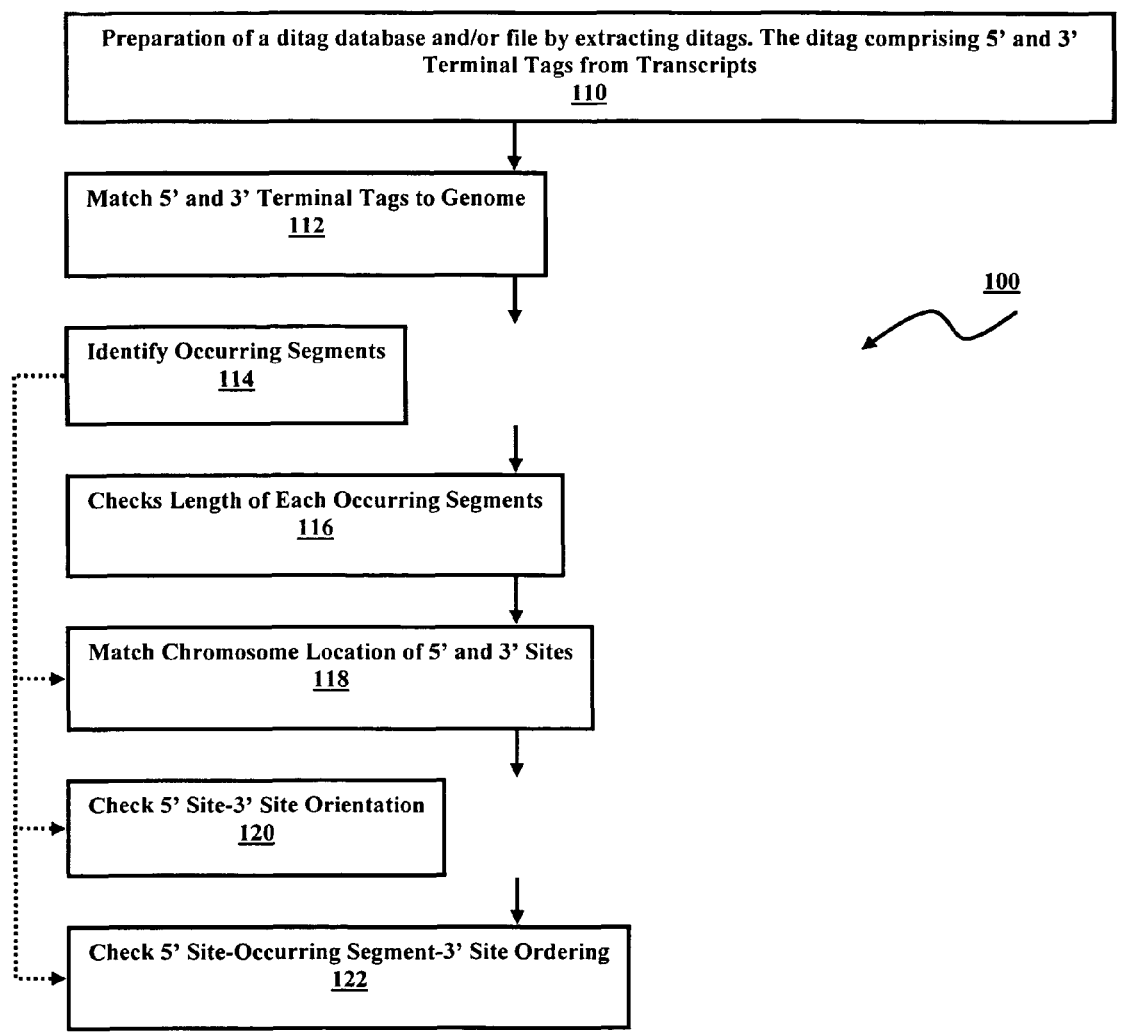
FIG. 3 shows a process flow chart of a transcript mapping method according to an embodiment of the invention.
Figure 4:
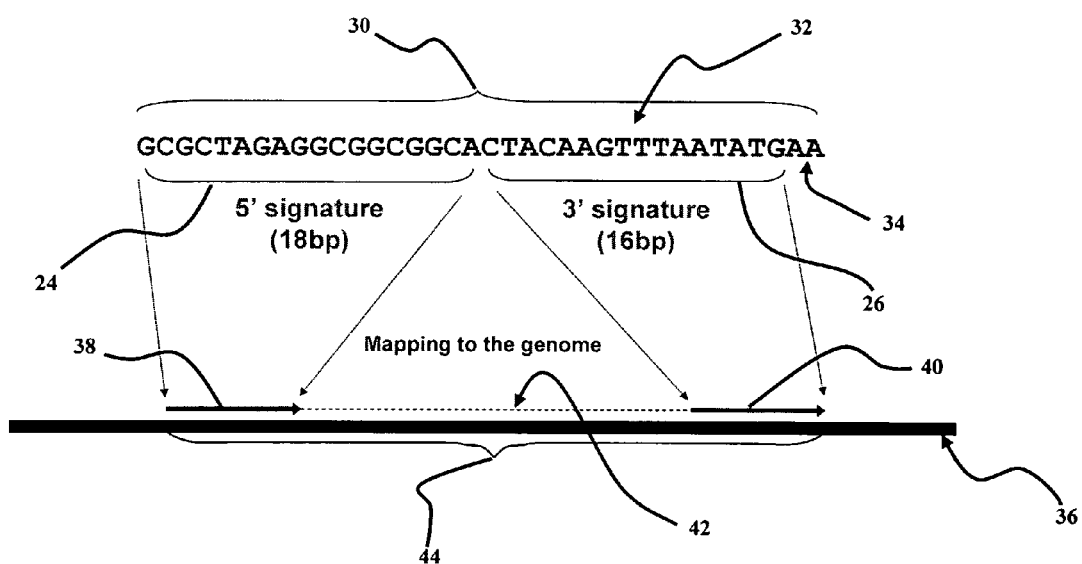
FIG. 4 shows a schematic diagram of a GIS ditag [SEQ ID NO: 1] for application of the transcript mapping technique of FIG. 3 thereto.

A first embodiment of the invention, a transcript mapping method 20 is described with reference to FIG. 3, which shows a process flow chart of the transcript mapping method 100. The transcript mapping method 100 is for application to a transcript obtained from a gene. In a step 110 of the transcript mapping method 100, a 5' terminal tag 24 and a 3' terminal tag 26 are obtained from the transcript, as can be seen in FIG. 4.

In combination, the 5' terminal tag 24 and the 3' terminal tag 26 forms a GIS ditag 30 as described above and as shown in FIG. 4. The GIS ditag 30 has a ditag length 32 of 36 bp with 18 bp nucleotide sequence being derived from the 5' terminal tag 24 and another 18 bp of nucleotide sequence being derived from the 3' terminal tag 26. Due to some enzymatic variations during molecular cloning, the ditag length 32 of the GIS ditag 30 may vary from 34 bp to 38 bp.

This variation often occurs proximate to the extremities of the 5' terminal tag 24 and the 3' terminal tag 26 with the internal nucleotides remaining structurally conserved. In the 3' terminal tag 26, two residual nucleotides 34 (AA) are retained during poly-A tail removal therefrom. The AA residual nucleotides 34 are subsequently for use as an orientation indicator. Therefore, only 16 bp of the 3' terminal tag 26 in the GIS ditag 30 is useful for mapping to a genome sequence 36.

Following the step 110, each of the 5' terminal tag 24 and the 3' terminal tag 26 is matched to the genome sequence 36 in a step 112. In the step 112, 5' sites 38 and 3' sites 40 are identified when the 5' terminal tag 24 and the 3' terminal tag 26 are respectively matched to the genome sequence 36. Each of the 5' sites 38 and each of the 3' sites 40 is a portion of the genome sequence 36 that has a sequence that substantially matches the 5' terminal tag 24 and the 3' terminal tag 26 respectively.

In a step 114, at least one occurring segment 42 is identified from the genome sequence 36. Each of the at least one occurring segment 42 is a sequence segment along the genome sequence 36 situated between one 5' site 38 and one 3' site 40. Each of the at least one occurring segment 42 has a sequence length 44.

Given the GIS ditag 30 (P) for the transcript (R), the computational problem of locating R in the genome sequence 36 (G) is referred to as a transcript location identification problem. Therefore, given G[1 ... n] and P[1 ... m], the occurring segment 42 is identified as being a feasible gene location of P when: the sequence length 44 (j−i) is smaller than the predefined gene length (maxlength), which is typically less than 1 million base pairs in length for known genes; the 5' terminal tag 24 and the 3' terminal tag 26 are longer than predefined $minlength_5$ and $minlength_3$ respectively (where $minlength_5$=16 bp and $minlength_3$=14 bp); and the 5' terminal tag 24 and the 3' terminal tag 26 of R are the substrings of P[1 ... $boundary_5$] and P[$boundary_3$ ... m] respectively (where $boundary_5$=19 and $boundary_3$=18).

The genome sequence 36 is preferably indexed using a compressed suffix array (CSA). The 5' terminal tag 24 and the 3' terminal tag are matched to the genome sequence 36 preferably by applying binary search to the compressed suffix array. The binary search for matching the 5' terminal tag 24 and the 3' terminal tag 26 are dependent on two lemmas, namely, lemma 1 for performing a forward search on the compressed suffix array and lemma 2 for performing a reverse search on the compressed suffix array.

Lemma 1 (forward search): given the CSA for the genome G[1 ... n] and a set of occurrences of a pattern Q in G, for any base c∈{adebine (A), cytosine (C), guanine (G), thymine (T)}, a set of occurrences of the pattern Qc is obtainable in O(log n) time. A forward binary search is achieved by modifying a conventional binary search algorithm to use values in the compressed suffix array and suffix array instead of explicit text for the suffixes in the genome sequence 36 when comparing with pattern Q in the binary search.

Lemma 2 (reverse search): given the CSA for the genome G[1 ... n] and a set of occurrences of a pattern Q in G, for any base c∈{A, C, G, T}, we can find the set of occurrences of the pattern cQ using O(log n) time.

The pseudo code "Find_Sites" for both the forward search and the reverse search is shown in FIG. 6. Instead of applying both the forward search and the reverse search in tandem in the step 114, an alternative approach is to apply either only the forward search using lemma 1 or only the reverse search using lemma 2 to the genome sequence 36 for identifying the at least one occurring segment 42.

The GIS ditag 30 may appear in the genome sequence 36 in sense or anti-sense. To address this issue, an index is created for each of the sense genome sequence and the anti-sense genome sequence. Instead of creating two separated indexing arrays, an anti-sense GIS ditag can be created. The suffix array is searched twice in the step 110 for each of the 5' terminal tag 24 and the 3' terminal tag 26, once using the sense GIS ditag 30 and a second time using the anti-sense GIS ditag (not shown).

Additionally, the genome sequence 36 can be naturally partitioned into chromosomes. This enables a compressed suffix array to be created for the sequence segment of each chromosome. By doing so, 5' sites 38 and 3' sites 40 are obtainable for specific chromosomes instead of the entire genome sequence 36.

Besides the compressed suffix array, a suffix array, a suffix tree, a binary or the like indexing data structure is usable for indexing the genome sequence 36 as abovementioned.

Following the step 114, the 5' sites 38 and the 3' sites 40 undergo a series of checks to identify a feasible gene location. The checks comprise length, locality, orientation and ordering checks.

In a step 116, the length check is performed by comparing the sequence length 44 of each of the at least one occurring segment 42 with a predefined gene length in a step 116. Initially, the 5' sites 38 and 3' sites 40 are sorted preferably in an ascending order. Next, each of the at least one occurring segment 42 has a sequence length 44 that does not exceed that of the predefined gene length (maxlength) is identified as a potential feasible gene location. The pseudo code "Match_sites_1" for step 116 is shown in FIG. 7.

In a step 118, the locality check is performed whereby the 5' site 38 and the 3' site 40 corresponding to each of the at least one occurring segment 42 are analysed to identify which chromosome each of them are located within. The occurring segment 42 identifies a potential feasible gene location only when the 5' site 38 and the 3' site 40 thereof belongs to the same chromosome.

In a step 120, the orientation check is performed by identifying the orientation of the 5' site 38 and the 3' site 40 that corresponds to each occurring segment 42. The orientation of the 5' site 38 and the 3' site is identifiable by locating the position of the residual nucleotide 34. Preferably, the 5' site 38 and the 3' site 40 should have a 5'-3' orientation for the occurring segment 42 thereof to identify a potential feasible gene location.

In a step 122, the ordering check is performed by comparing each of the occurring segments 42 and the corresponding 5' site 38 and 3' site 40 to the genome sequence 36. Preferably, the ordering of each of the occurring segments 42 and its corresponding 5' site 38 and 3' site 40 should follow a 5'-occurring segment-3' structure for it to be a potential feasible site.

Steps 116-122 of the transcript mapping method can occur in any sequence in combination or independently.

In a situation where the feasible gene location is not found from the GIS ditag 30, the constraints are relaxed to allow at least one mismatch when matching the 3' terminal tag 26 to the genome sequence 36 in the step 112.

Alternatively, the quantity of the 5' sites 38 and the quantity of the 3' sites 40 are initially obtained before the 5' sites 38 and the 3' sites 40 are matched to the genome sequence 36 in the step 112. This enables identification of quantity disparity between the 5' sites 38 and the 3' sites 40, for example, when there only exist less than ten of the 5' sites 38 and more than tens of thousand of the 3' sites 40, or vice versa.

When large quantity disparity between the 5' sites 38 and the 3' sites 40 exists, the transcript mapping method 20 undergoes multiple iterations of redundant mapping to the genome sequence 36. Therefore, a modified approach is required for the transcript mapping method 100 when a large quantity disparity arises. To identify the quantity disparity, a disparity condition is established as:

$$\frac{1}{threshold_{5,3}} \geq \frac{count_5}{count_3} \geq threshold_{5,3}$$

where $count_5$ is the quantity of 5' sites 38, $count_3$ is the quantity of 3' sites 40, and $threshold_{5,3}$ is a pre-defined threshold, for example $threshold_{5,3}$=10,000, for limiting the quantitative disparity between $count_5$ and $count_3$. The CSA enables both $count_5$ and $count_3$ to be obtained without enumerating either any of the 5' sites 38 or any of the 3' sites.

The method described in the pseudo code "Match_sites_2" of FIG. 8 is applied when the above disparity condition is met. In the pseudo code "Match_sites_2", the number of iterations required for mapping to the genome sequence 36 is determined by the smaller one of $count_5$ and $count_3$. For example, should there be only two 5' sites 38, the mapping to or traversal along the genome sequence 36 for obtaining the corresponding one of the 3' sites 40 is only iterated twice, once for each of the two 5' sites 38, for obtaining the occurring segments 42 therefrom.

However, should the above disparity condition be unmet, the quantity disparity between $count_5$ and $count_3$ is not large and therefore the transcript mapping method 100 reverts to the method described in "Match_sites_1" for obtaining the occurring segments 42.

In the foregoing manner, a transcript mapping method is described according to one embodiment of the invention for addressing the foregoing disadvantages of conventional mapping methods. Although only one embodiment of the invention is disclosed, it will be apparent to one skilled in the art that numerous changes and/or modification can be made without departing from the scope and spirit of the invention.

Having now generally described the invention, the same will be more readily understood through reference to a particular embodiment, which is referred to GISditagTool, with the assistance of the following Figures which are provided by way of illustration, and are not intended to be limiting of the present invention.

GISditagTool—SYSTEM AND METHODS

1. Data Management

Figure 9:
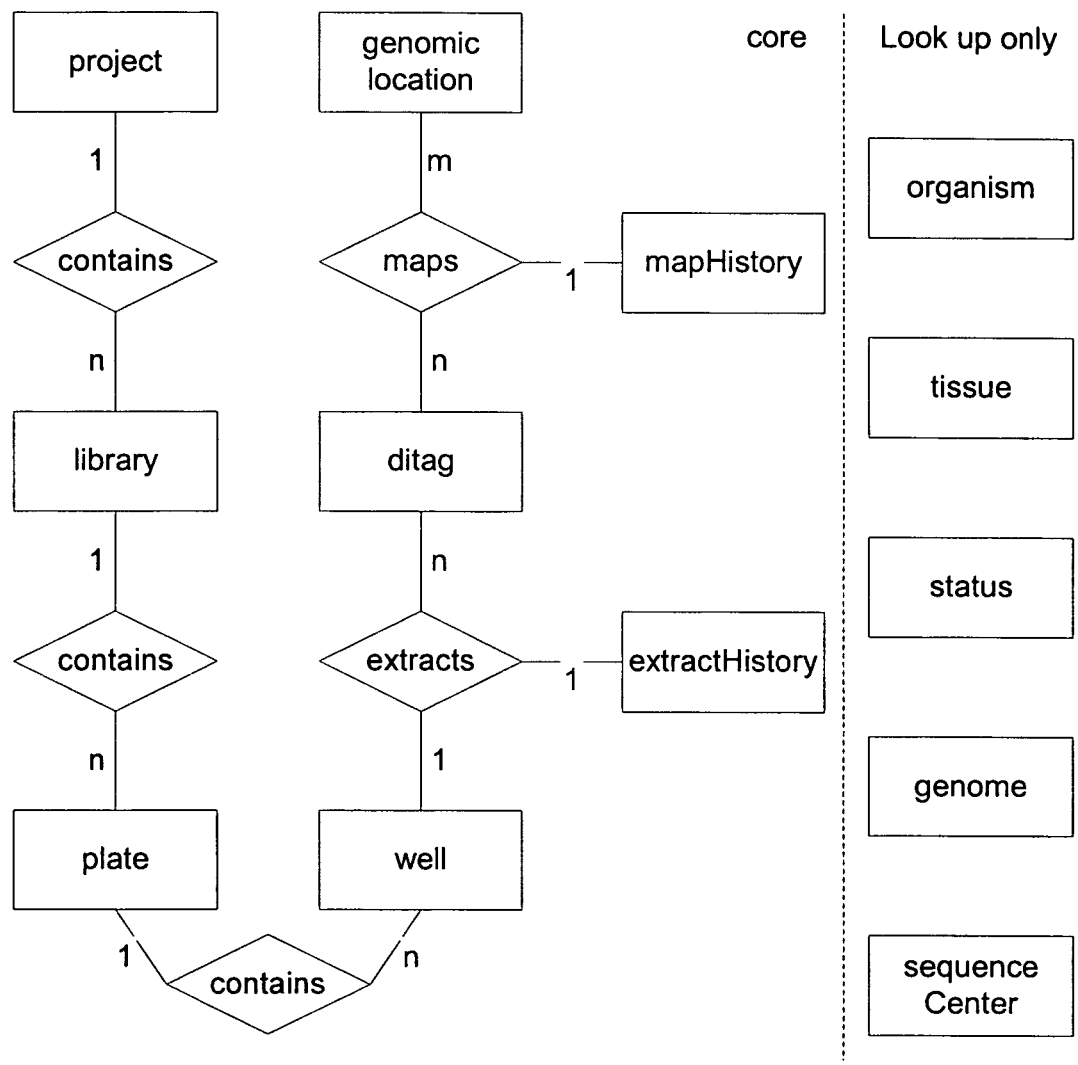
FIG. 9. Data Management. Entity-relationship diagram of GISditagTool. The entity-relationship depicts the architecture of the mySQL tables. The architecture is composed of project, library, plate, well (each representing a sequence), ditag, and genomic location in sequential order. The extractHistory and mapHistorytables record the activities of ditag extraction and mapping, respectively. The organism, tissue, status, genome, and sequencecenter tables provide background information needed for the process.

To fulfil the requirement for large scale data analysis, data and results may be organized in a hierarchical framework of project, library, plate and well, attached with records of actions and their corresponding parameters (FIG. 9). A hybrid of flat file system and RDBMS may be used based on data characteristics. Uploaded sequence reads may be stored as flat file with positional index recorded in the RDBMS to support quick retrieval. The remaining information and processed results may be kept in RDBMS to facilitate querying. These include the various statistical, progress and tracking attributes and mapping results.

Figure 10:
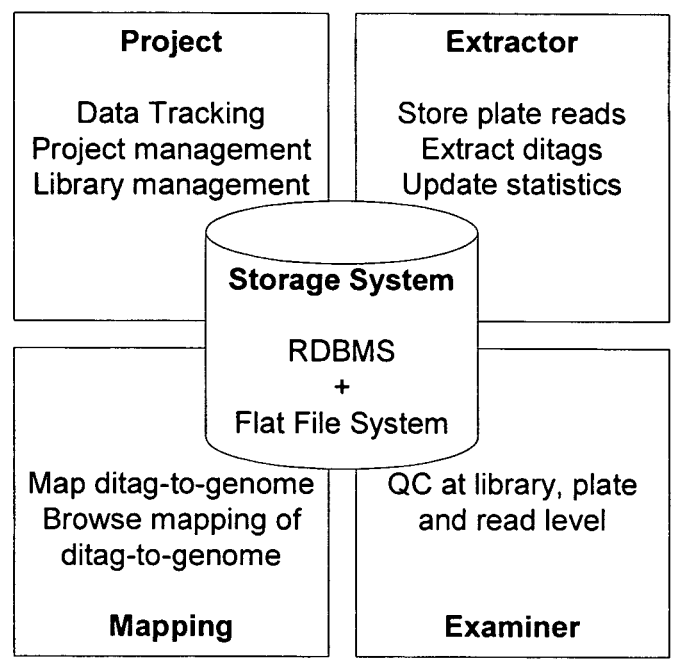
FIG. 10. GISditagTool modules and mySQL database. According to one embodiment, the GISditagTool comprises four modules, namely Project, Extractor, Examiner and Mapping. Each one of them serves a distinct purpose: Project is for data and file organization; Extractor for ditag extraction; Examiner for quality control; and Mapping for tag-to-genome mapping. mySQL rational DB management system provides easy trafficking for the activities between those modules.

GISditagTool modules and mySQL database are shown in FIG. 10. GISditagTool may comprise one or more modules. In particular, GISditagTool may comprise two or more modules, for example, four modules: namely Project, Extractor, Examiner and Mapping. Each one of them serves a distinct purpose: Project is for data and file organization; Extractor is for ditag extraction; Examiner is for quality control; and Mapping is for tag-to-genome mapping. The use of mySQL rational DB management system may provide easy trafficking for the activities between those modules.

2. GISditag (PET) Analysis Work Flow, Methods and Systems

A complete GIS ditag analysis work flow comprises, for example, five sequential steps: 1) User creates a project and then a library or libraries in the project. Library-specific information, including extraction and mapping parameters, are entered. 2) Sequences in a single or multiple files are uploaded from a local terminal into a corresponding library and ditags are extracted from the sequences using parameters defined previously. This step also allows the user to change parameters. 3) Quality control (QC) that can be conducted at project, library, plate, well/sequence, or ditag level. 4) Ditags are then subjected to mapping against UCSC genomic database, for example by using SAT2G, and mapping result displayed in UCSC graphic format. 5) With the mapping results, ditags are annotated against a corresponding database.

Steps 1-4 are handled by GISditagTool with Project, Extractor, Examiner and Mapping modules, respectively. Step 5 may be incorporated into the GISditagTool or carried out as a supplementary and independent step.

Figure 11:
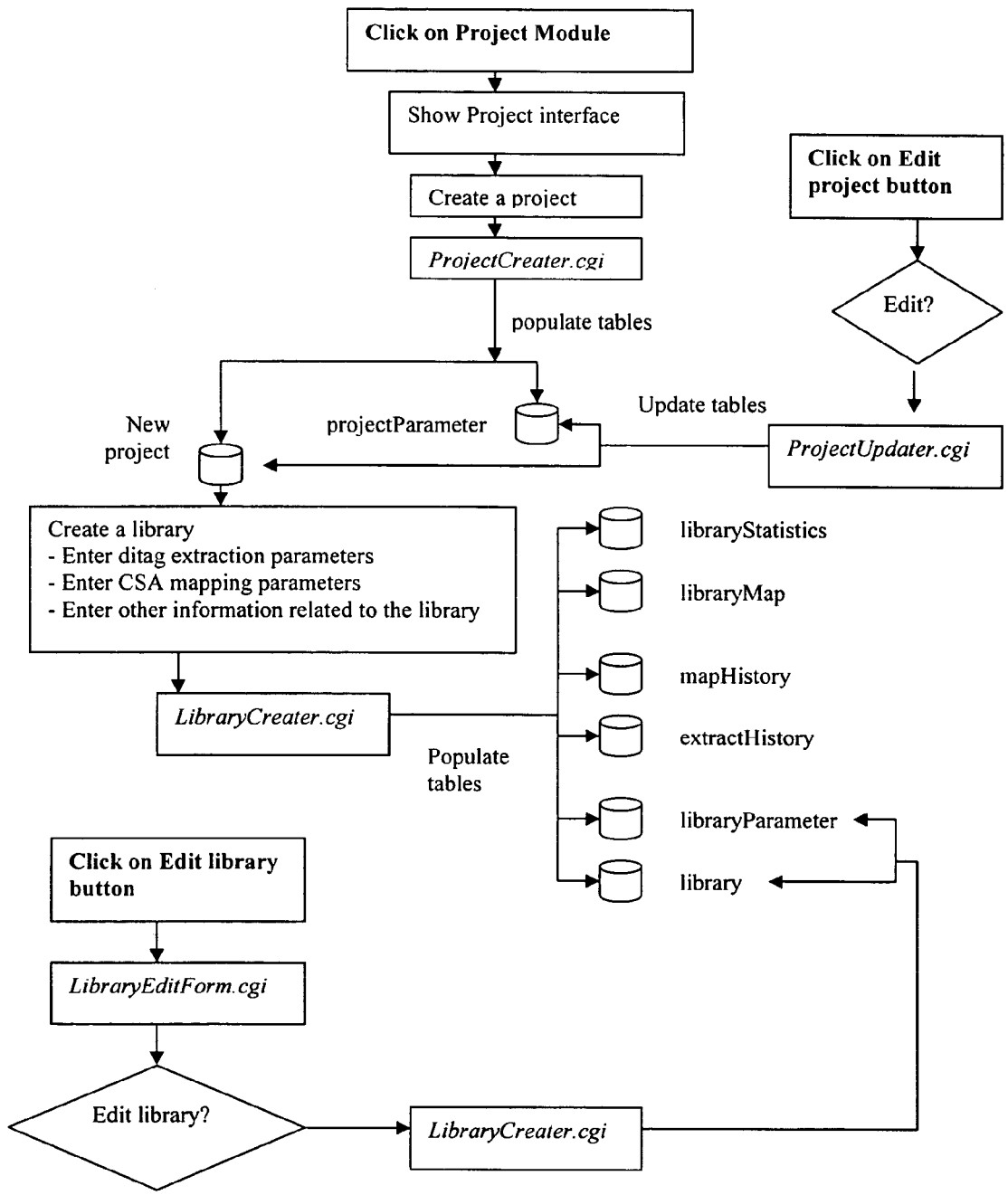
FIGS. 11 to 14 show Flow Charts of four GISditagTool modules according to one aspect of the invention. In particular.
Figure 12:
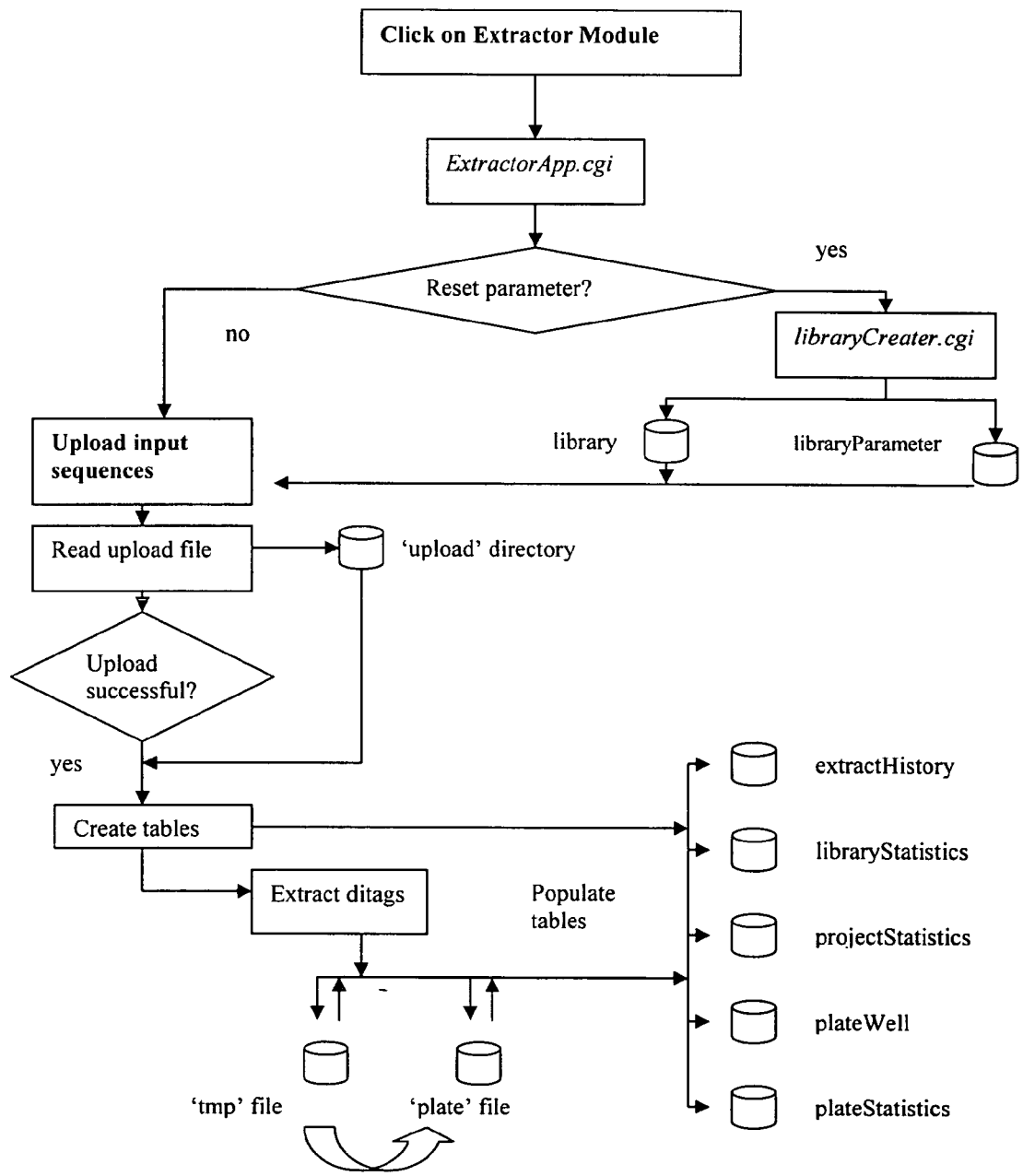
Figure 13:
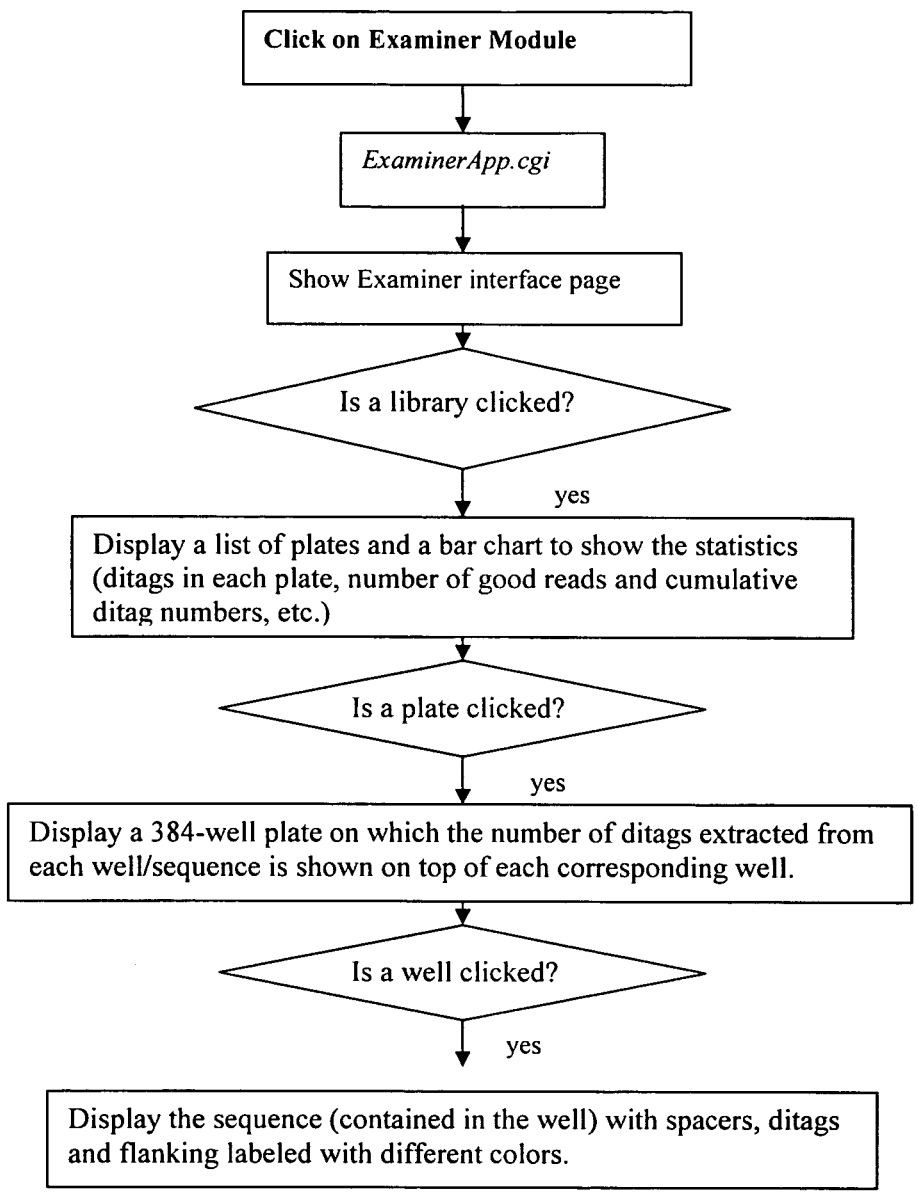
Figure 14:
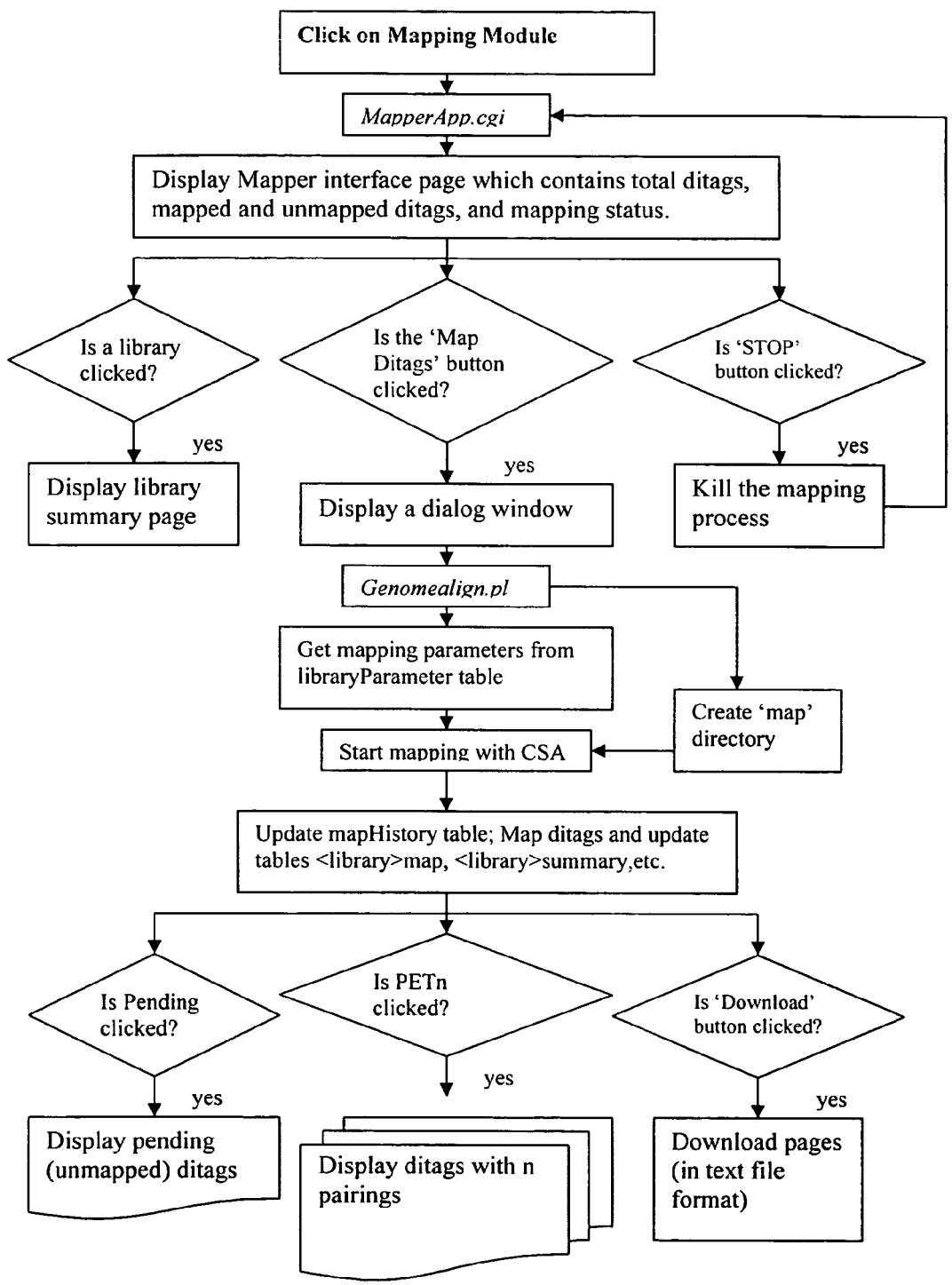
Figure 18:
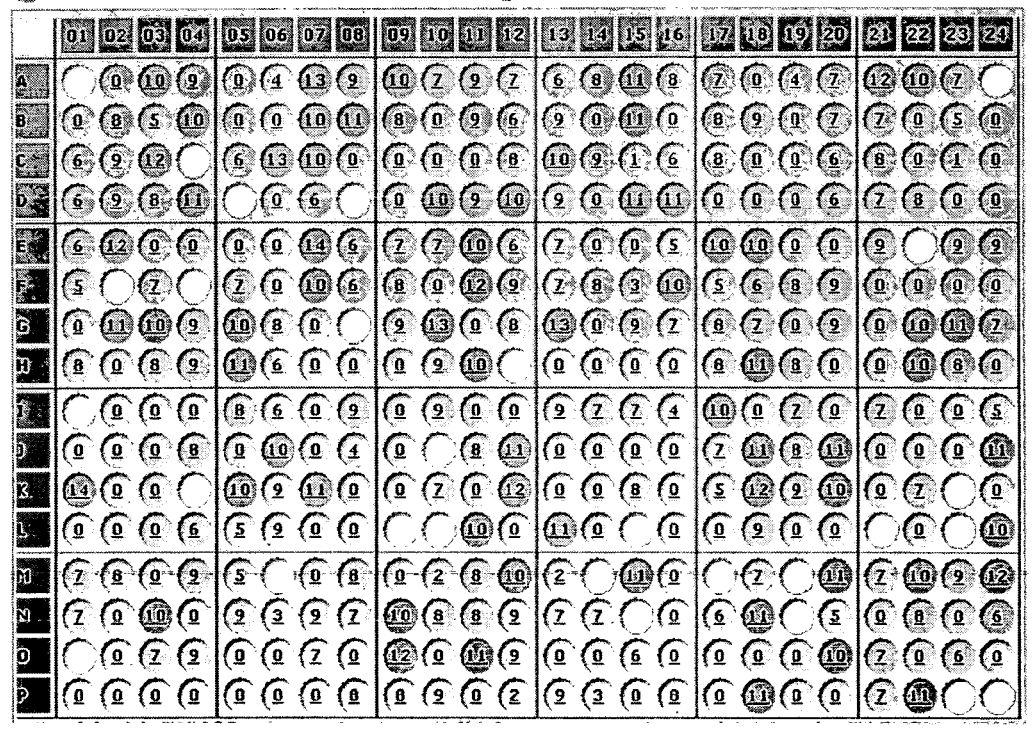
FIG. 18 shows the user interface (E) of GISditagTool of FIG. 15.

Flow Charts of four GISditagTool modules are shown in FIGS. 11 to 14. In particular, FIG. 11 shows a Project Module flow chart, FIG. 12 shows an Extractor Module flow chart, FIG. 13 shows an Examiner Module flow chart, and FIG. 14 shows a Mapping Module flow chart.

3. Ditag Extraction

Figure 15:
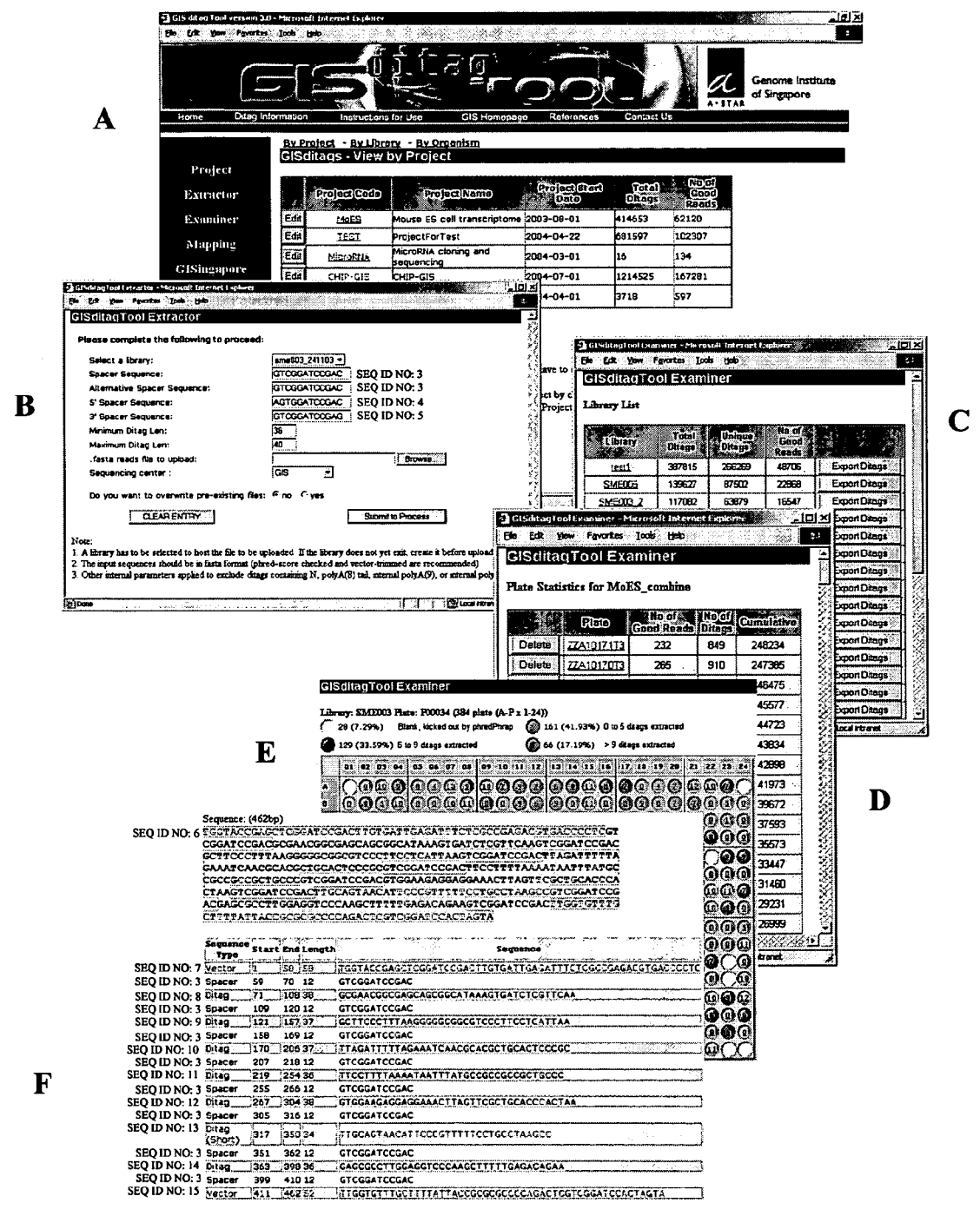
Figure 16:
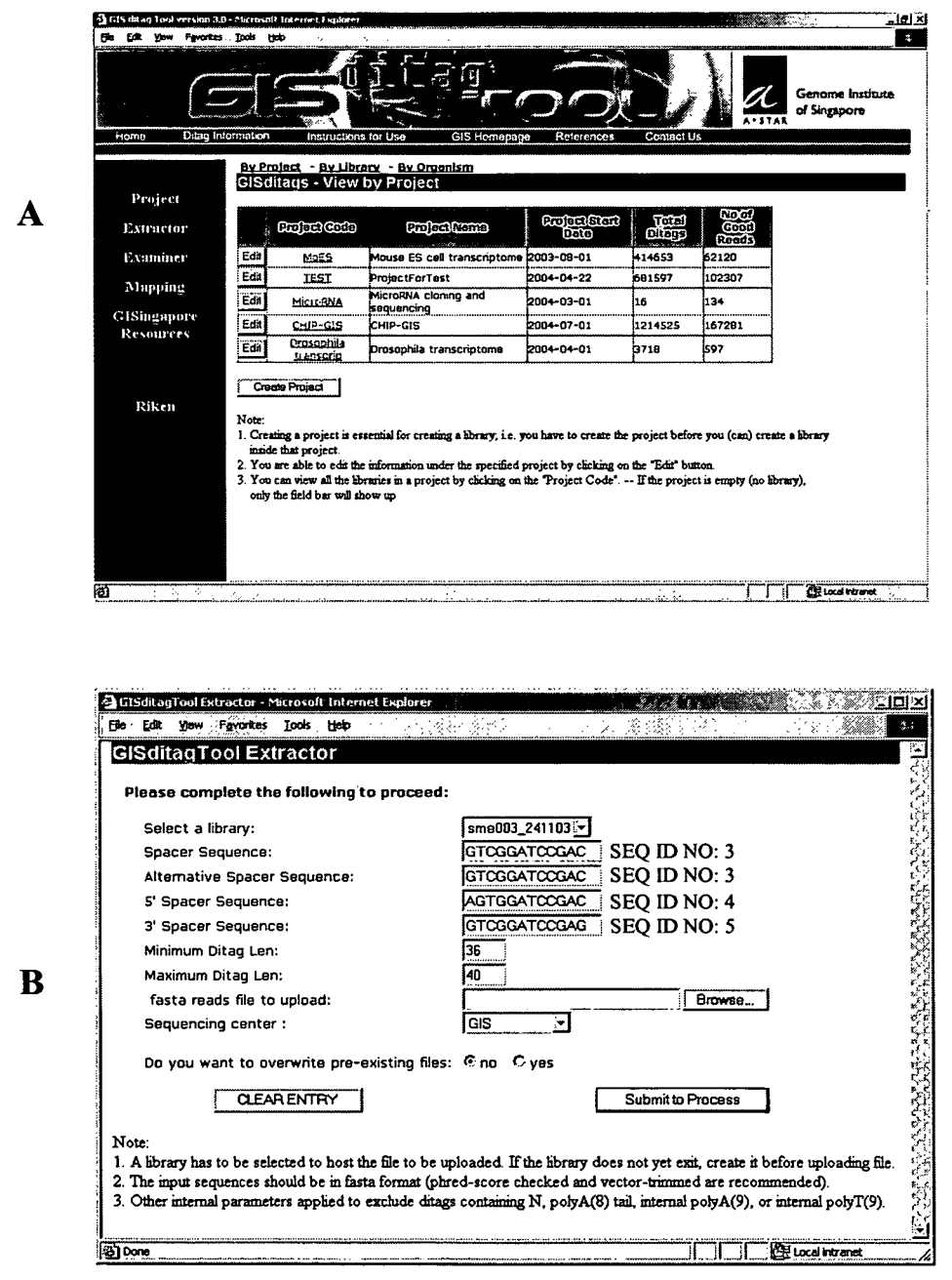

The extractor module flow chart is shown in FIG. 11. Extraction and quality control (QC) windows and user interfaces of GISditagTool are shown in FIG. 15. Sequence reads can be uploaded for ditag extraction via the extractor module (B) (also shown in FIG. 16). The extraction parameters can be modified at this stage. QC is conducted in sequential order. The very top panel (A) of FIG. 15 shows the statistics of all the projects (also shown in FIG. 16). When the Examiner module is activated, ditag statistics for all the libraries is shown (C). Clicking on a library, a plate in a library, and then a well in a plate, the user is able to evaluate the quality of plates (D), wells (E), and sequence (F), respectively.

Input sequences (in fasta format) are base called and scored with phredPhrap to ensure quality. The fasta format is the major format used in the scientific community for sequence data processing (http://ngfnblast.gbf.de/docs/fasta.html). Phred and Phrap were generated and are continuously being improved or modified by Phil Green's group at University of Washington (http://www.phrap.org/phredphrap/phrap.html). Sequence ID traditionally comprises information of library, plate, well, sequencing primer, etc. to formulate a unique combination; however, the order and characters may vary among different institutions. To accommodate sequence naming convention of different affiliations, the system stored a named Perl snippet for each affiliation for proper sequence ID retrieval. During ditag extraction, new unique ditags are assigned with a running serial numbers incrementally to prevent ID conflicts with ditags that may be extracted in the future uploads. Extraction algorithm includes the following selection criteria or parameters: minimal ditag length, 34 bp; maximal ditag length, 40 bp; maximal sequence length, 1000 bp; and defined 5', 3' and internal spacer sequences that separate the ditags (FIG. 15-B). All qualified ditags should have an AA-tail at the 3' end. We reverse ditags starting with 'TT' to their respective complementary strands because they are sequenced from the opposite strand. Ditags containing either polyA (9 bp) or polyT (9 bp) in either the 5' or 3' tag region are removed because they are either contaminants or real sequences but possess potential mapping difficulty. Ditags that containing 'N' are also removed. Finally, the AA-tail is removed to prevent complication in mapping.

4. Quality Control

Quality control aims to evaluate the extraction results at various levels to provide clues that may help pinpoint problems in wet-lab material, protocol or technique. It is conducted by using the "Examiner" module. At the project level (FIG. 15-A), it displays the project starting date, total good reads and total ditags for each project. At the library level (FIG. 15-C, and FIG. 17-C), the interface displays information regarding the total numbers of good reads, unique ditags and total ditags that have been extracted for each library. A quick glimpse can tell the status and performance of a library as well as the differences among various libraries. For deeper quality checking, the user is allowed to click on a particular library to display all the plates for that library (FIGS. 15-D and 17-D). Here, statistics is on plate basis. If the user is not satisfied with the quality, the user can delete any plate and the system will instantly update the change. When a particular plate is selected, GISditagTool displays a vivid view of all 384 wells (represent corresponding sequences) on which the numbers of extracted ditags are shown (FIGS. 15-E and 18-E). Clicking on a well, one can get a closer look of the distribution of the 5' and 3' flanking regions, spacers, and both qualified and unqualified ditags (FIGS. 15-F and 19-F).

5. Mapping

Figure 20:
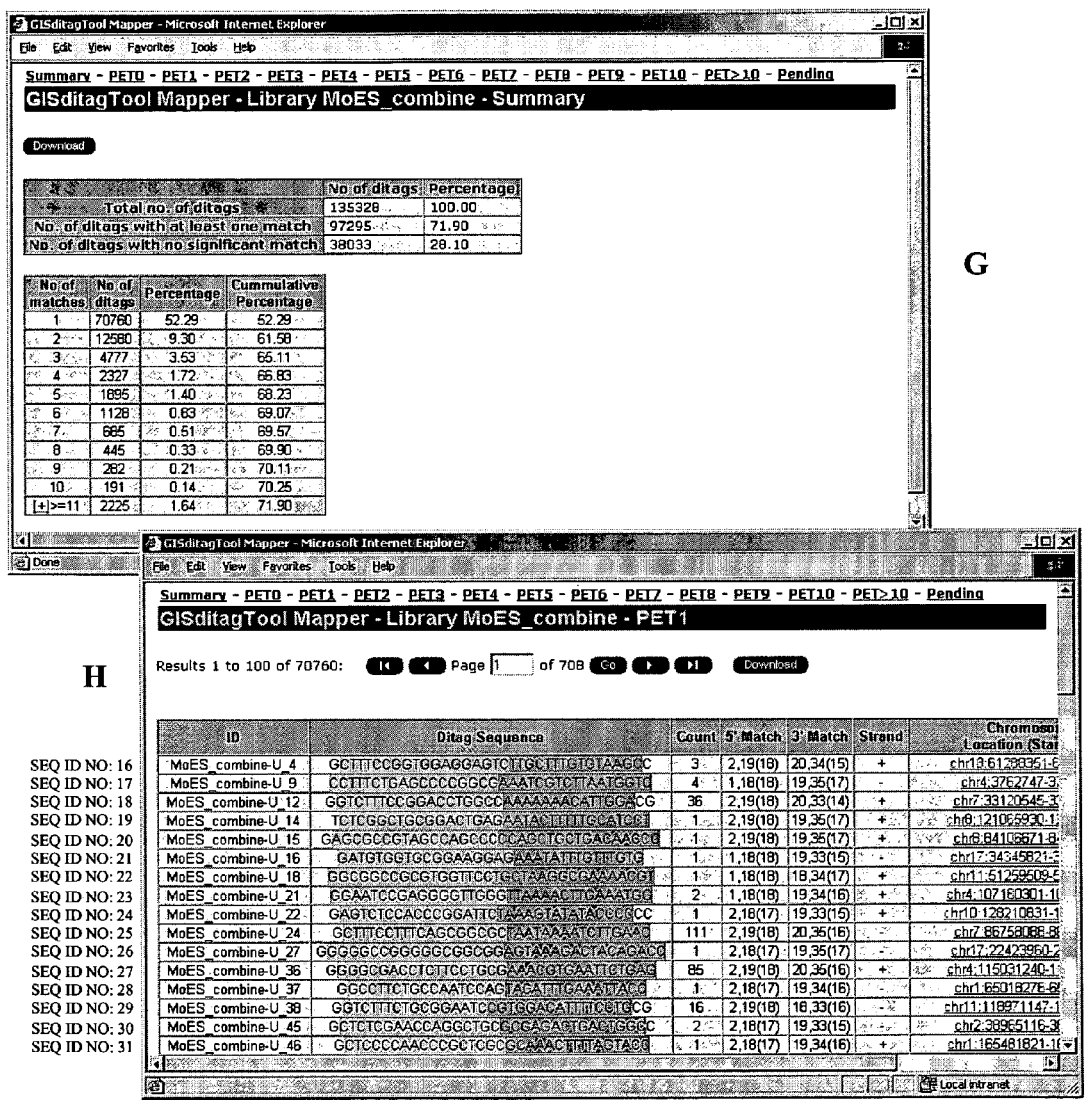
FIG. 20. Mapping result shown in GISditagTool. User interfaces (G) and (H). The mapping module aligns the ditags to genome and provides both the mapping summary (G) and browsing capability (H) via UCSC browser. Ditags are grouped into various categories (e.g. PET0, PET1, PET2, etc.) based on the number of targets found in the genome.

The present inventors adopted SAT2G for mapping due to its speed and accuracy. The inventors define subsequences of the 5' tag as the first 18±1 bp and allow them to start from position 1, 2, or 3. The remaining portions of the ditag form the 3' tag subsequences. These subsequences are mapped to genomic database independently. The 5' alignments are then paired with the 3' alignments to identify the plausible genomic target(s) (FIG. 5). A successful pairing has to meet the following criteria: the 5' and 3' alignments have to be in the same chromosome, same strand, same orientation, within 1 million bp, and in 5' followed by 3' order; and the 5' and 3' alignments need to have at least 16 and 14 bp perfect matches, respectively. Ditags with no successful pairing are collected in PET0, single pairing in PET1, double pairings in PET2, etc (FIG. 20-G). As expected, the above parameter setting will push ditags generated by non-canonical processing (such as trans-splicing) into PET0 category; however, these ditags can later on be retrieved from PET0 for further analysis.

The mapped locations may be linked to a local or remote UCSC genome browser for gene annotation and other related information (FIG. 20-H). Alternatively, a user may perform further analysis using other databases. In our case, these ditags are further associated with genes or transcripts using T2G pipeline with a mirrored UCSC annotation database. These associations are accessible from T2G web site using localized UCSC genome browser.

Ditag extraction and/or storage in RDBMS and genome mapping with SAT2G are relevant functions of the GISditagTool. RDBMS provides fast and efficient data trafficking. SAT2G contributes a great mapping power to GISditagTool. With a regular 750 Mhz Solaris machine, handling 100 K ditags would require about 2 months for BLAST (without pairing) while CSA takes just a few hours under the same or similar mapping criteria exercised. Such speed allows efficient data analysis. Besides, GISditagTool allows and supports the mapping of each ditag library to different genome assemblies. The user can use a newly available genome assembly while retaining the earlier mapping for comparison. The direct PET-to-genome mapping approach not only bypasses the need for a virtual database, it also allows the discovery of new genes because chromosome locations can be linked to databases for further data mining.

6. Results

The present inventors have thus developed GISditagTool, which is a multi-component, web-based, database supported (for example, mySQL-supported) application for large-scale ditag (PET) processing and genome mapping. It comprises two or more modules, preferably four modules: Project for data organization, Extractor for ditag extraction, Examiner for quality control, and Mapping for identification of PETs' chromosome locations using a mapping system, for example SAT2G (suffix array-based tag-to-genome). Data quality can be evaluated at library, plate, well, sequence and ditag levels. It is capable of extracting one million PETs and finishing genome mapping in one day. Mapping results can be displayed in any known genome browser, for example, the UC Santa Cruz (UCSC) genome browser.

This novel GISditagTool technology requires a new algorithm for PET extraction in the form of parameters. The parameters comprise at least: a minimal ditag length, a maximal ditag length and the sequence of the spacer. Post extraction, we intended to take a direct PET-to-genome-to-annotation approach and integrate the algorithms in a software program package.

GISditagTool has been used to analyze over 20 libraries generated from various organisms. Using a mouse embryonic stem cell line as an example, a total of 248,234 ditags, equivalent to 135,328 unique ditags, were extracted from 37,754 sequence reads. Without allowing mismatches, 71.90% of the total ditags have been successfully mapped to locations in UCSC mouse genome assembly mm3 and 52.29% of the total ditags have single mapping locations. In practice, GISditagTool has demonstrated an extraordinary and reliable performance and is very user-friendly.

The invention claimed is:

1. A method of processing ditag nucleotide sequence(s) for mapping the ditag nucleotide sequence(s) to a genome, the ditag sequence comprising the 5' terminal tag and the 3' terminal tag of a nucleic acid molecule or fragment thereof or genomic fragment, the method comprising
(i) preparing a database or file comprising at least one ditag sequence by extracting the ditag sequence(s) from sequences of at least one library comprising ditags, wherein each ditag sequence of the library of ditag(s) is flanked by a spacer nucleotide sequence and each ditag sequence is extracted from the library by inputting the spacer nucleotide sequence(s);
(ii) matching the 5' terminal tag to at least a portion of a genome sequence to identify at least one 5' site having a sequence matching the 5' terminal tag;
(iii) matching the 3' terminal tag to at least a portion of a genome sequence to identify at least one 3' site having a sequence matching the 3' terminal tag;
(iv) identifying at least one occurring segment comprising a sequence segment along the genome sequence between one 5' site and one 3' site, each occurring segment having a sequence length; and
(v) identifying at least one gene location comprising at least one occurring segment having a sequence length not exceeding that of a predefined gene length; wherein the extraction of ditag sequence(s), the genome mapping or both the extraction of ditag sequences and the genome mapping is/are carried out on a computer.

2. The method according to claim 1, wherein the library of ditag(s) comprises at least a concatemer of two or more ditags, the concatemer comprising, in a 5'-3' orientation, a spacer flanking upstream the first ditag, a spacer flanking downstream the last ditag, and wherein each two neighbouring ditags are separated by a spacer positioned between them.

3. The method according to claim 1, wherein the library of ditag(s) comprises one or more spacer sequences, each spacer sequence having a different nucleotide sequence from the other(s).

4. The method according to claim 1, wherein the ditag sequence(s) is extracted by inputting the following parameters:
at least one spacer nucleotide sequence;
a minimal ditag base pair (bp) digit, wherein the digit is a number chosen from the range of 32-38; and
a maximal ditag base pair (bp) digit, wherein the digit is a number chosen from the range of 36-42.

5. The method according to claim 4, wherein the minimal ditag base pair digit is 34 and/or the maximal ditag base pair digit is 40.

6. The method according to claim 1, wherein the ditag sequence comprises the 5' terminal tag and the 3' terminal tag of a transcript of a gene, exon, a portion of the genome, or fragment thereof.

7. The method of claim 1, wherein the ditag sequence comprises the 5' terminal tag and the 3' terminal tag of a full-length cDNA.

8. The method according to claim 1, wherein the ditag sequence(s) comprises a 5' terminal tag of at least 16 base pairs and a 3' terminal tag of at least 14 base pairs.

9. The method according to claim 1, wherein the method further comprises carrying out a quality control check of the ditag sequences of the database or file.

10. The method according to claim 1, wherein the identified gene location is a newly discovered gene location.

11. A computer for processing ditag nucleotide sequence(s), the ditag sequence comprising the 5' terminal tag and the 3' terminal tag of a nucleic acid molecule, or fragment thereof or genome fragment, comprising at least one program, wherein the at least one program
(i) prepares a database or file comprising at least one ditag sequence by extracting the ditag sequence(s) of at least one library comprising ditag(s), wherein each ditag sequence of the library of ditag(s) is flanked by a spacer nucleotide sequence and each ditag sequence is extracted from the library by inputting the spacer nucleotide sequence(s);
(ii) matches the 5' terminal tag to at least a portion of a genome sequence to identify at least a 5' site having a sequence matching the 5' terminal tag;

(iii) matches the 3' terminal tag to at least a portion of the genome sequence to identify at least a 3' site having a sequence matching the 3' terminal tag;
(iv) identifies at least one occurring segment comprising a sequence segment along the genome sequence between one of the 5' site and one of the 3' site, each occurring segment having a sequence length; and
(v) identifies at least one gene location comprising at least one occurring segment having a sequence length not exceeding that of a predefined gene length.

12. The computer of claim 11, wherein each ditag sequence of the library of ditag(s) is flanked by a spacer nucleotide sequence and the ditag sequence(s) is extracted from the library by inputting the spacer nucleotide sequence(s).

13. The computer according to claim 12, wherein an operator selects at least a link, which activates the module, the module launching at least a user interface, and wherein the operator inputs into the user interface the following parameters:
   at least one spacer nucleotide sequence;
   a minimal ditag base pair (bp) digit, wherein the digit is a number chosen from the range of 32-38; and
   a maximal ditag base pair (bp) digit, wherein the digit is a number chosen from the range of 36-42; thereby creating a database or file of extracted ditag(s).

14. The computer according to claim 13, wherein the minimal ditag base pair digit is 34 and/or the maximal ditag base pair digit is 40.

15. The computer according to claim 11, wherein the ditag sequence comprises the 5' terminal tag and the 3' terminal tag of a transcript of a gene, exon, a portion of the genome, or fragment thereof.

16. The computer according to claim 11, further comprising a module of quality control of the database or file of ditag sequences.

17. The computer according to claim 11, comprising at least the following:
   a first user interface comprising at least a link for extracting (extractor) the ditag sequences and a link for mapping the ditag to a genome;
   a second user interface, which is activated by an operator by selecting or clicking on the extractor, the second user interface comprising fields for inputting a minimal ditag base pair (bp) digit, a maximal ditag base pair (bp) digit, and the nucleotide sequence of at least one spacer sequence;
   a third user interface for mapping the ditag sequence(s) to the genome; and
   a fourth user interface showing the results of the mapping, wherein the ditag(s) is aligned to genome.

18. The computer according to claim 11, wherein the system is operable by an operator on a computer and the operation is carried out through the Internet, on a computer and/or of a medium support.

* * * * *

```
                        SEQUENCE LISTING

<160> NUMBER OF SEQ ID NOS: 31

<210> SEQ ID NO 1
<211> LENGTH: 36
<212> TYPE: DNA
<213> ORGANISM: Mus musculus

<400> SEQUENCE: 1
gcgctagagg cggcggcact acaagtttaa tatgaa                                 36

<210> SEQ ID NO 2
<211> LENGTH: 37
<212> TYPE: DNA
<213> ORGANISM: Mus musculus

<400> SEQUENCE: 2
gccttttcct gtgggagcaa acatgtggtg acaagaa                                37

<210> SEQ ID NO 3
<211> LENGTH: 12
<212> TYPE: DNA
<213> ORGANISM: Mus musculus

<400> SEQUENCE: 3
gtcggatccg ac                                                           12

<210> SEQ ID NO 4
<211> LENGTH: 12
<212> TYPE: DNA
<213> ORGANISM: Mus musculus

<400> SEQUENCE: 4
agtggatccg ac                                                           12

<210> SEQ ID NO 5
<211> LENGTH: 12
<212> TYPE: DNA
<213> ORGANISM: Mus musculus

<400> SEQUENCE: 5
gtcggatccg ag                                                           12

<210> SEQ ID NO 6
<211> LENGTH: 462
<212> TYPE: DNA
<213> ORGANISM: Mus musculus
```

<400> SEQUENCE: 6

```
tggtaccgag ctcggatccg acttgtgatt gagatttctc gccgagacgt gacccctcgt    60
cggatccgac gcgaacggcg agcagcggca taaagtgatc tcgttcaagt cggatccgac   120
gcttcccttt aaggggcgg cgtcccttcc tcattaagtc ggatccgact tagattttta   180
gaaatcaacg cacgctgcac tcccgcgtcg gatccgactt cctttaaaa taatttatgc   240
cgccgccgct gcccgtcgga tccgacgtgg aagaggagga aacttagttc gctgcaccca   300
ctaagtcgga tccgacttgc agtaacattc ccgttttttcc tgcctaagcc gtcggatccg   360
acgagcgcct tggaggtccc aagcttttg agacagaagt cggatccgac ttggtgtttg   420
cttttattac cgcgcgcccc agactcgtcg gatccactag ta                       462
```

<210> SEQ ID NO 7
<211> LENGTH: 58
<212> TYPE: DNA
<213> ORGANISM: Mus musculus

<400> SEQUENCE: 7

```
tggtaccgag ctcggatccg acttgtgatt gagatttctc gccgagacgt gacccctc      58
```

<210> SEQ ID NO 8
<211> LENGTH: 38
<212> TYPE: DNA
<213> ORGANISM: Mus musculus

<400> SEQUENCE: 8

```
gcgaacggcg agcagcggca taaagtgatc tcgttcaa                             38
```

<210> SEQ ID NO 9
<211> LENGTH: 37
<212> TYPE: DNA
<213> ORGANISM: Mus musculus

<400> SEQUENCE: 9

```
gcttcccttt aaggggcgg cgtcccttcc tcattaa                               37
```

<210> SEQ ID NO 10
<211> LENGTH: 37
<212> TYPE: DNA
<213> ORGANISM: Mus musculus

<400> SEQUENCE: 10

```
ttagattttt agaaatcaac gcacgctgca ctcccgc                              37
```

<210> SEQ ID NO 11
<211> LENGTH: 36
<212> TYPE: DNA
<213> ORGANISM: Mus musculus

<400> SEQUENCE: 11

```
ttccttttaa aataatttat gccgccgccg ctgccc                               36
```

<210> SEQ ID NO 12
<211> LENGTH: 38
<212> TYPE: DNA
<213> ORGANISM: Mus musculus

<400> SEQUENCE: 12

```
gtggaagagg aggaaactta gttcgctgca cccactaa                             38
```

```
<210> SEQ ID NO 13
<211> LENGTH: 34
<212> TYPE: DNA
<213> ORGANISM: Mus musculus

<400> SEQUENCE: 13
ttgcagtaac attcccgttt ttcctgccta agcc                         34

<210> SEQ ID NO 14
<211> LENGTH: 36
<212> TYPE: DNA
<213> ORGANISM: Mus musculus

<400> SEQUENCE: 14
gagcgccttg gaggtcccaa gcttttttgag acagaa                      36

<210> SEQ ID NO 15
<211> LENGTH: 52
<212> TYPE: DNA
<213> ORGANISM: Mus musculus

<400> SEQUENCE: 15
ttggtgtttg cttttattac cgcgcgcccc agactcgtcg gatccactag ta     52

<210> SEQ ID NO 16
<211> LENGTH: 35
<212> TYPE: DNA
<213> ORGANISM: Mus musculus

<400> SEQUENCE: 16
gctttccggt ggaggagtct tgctttgtgt aagcc                        35

<210> SEQ ID NO 17
<211> LENGTH: 35
<212> TYPE: DNA
<213> ORGANISM: Mus musculus

<400> SEQUENCE: 17
cctttctgag ccccggcgaa atcgtcttaa tggtc                        35

<210> SEQ ID NO 18
<211> LENGTH: 35
<212> TYPE: DNA
<213> ORGANISM: Mus musculus

<400> SEQUENCE: 18
ggtctttccg gacctggcca aaaaaacatt ggacg                        35

<210> SEQ ID NO 19
<211> LENGTH: 35
<212> TYPE: DNA
<213> ORGANISM: Mus musculus

<400> SEQUENCE: 19
tctcggctgc ggactgagaa tactttttgc atcct                        35

<210> SEQ ID NO 20
<211> LENGTH: 35
<212> TYPE: DNA
<213> ORGANISM: Mus musculus

<400> SEQUENCE: 20
gagcgccgta gccagccccc agctgctgac aaccc                        35
```

```
<210> SEQ ID NO 21
<211> LENGTH: 33
<212> TYPE: DNA
<213> ORGANISM: Mus musculus

<400> SEQUENCE: 21
gatgtggtgc ggaaggagaa atatttgttt gtg                              33

<210> SEQ ID NO 22
<211> LENGTH: 34
<212> TYPE: DNA
<213> ORGANISM: Mus musculus

<400> SEQUENCE: 22
ggcggccgcg tggttcctgc taaggcgaaa acgt                             34

<210> SEQ ID NO 23
<211> LENGTH: 34
<212> TYPE: DNA
<213> ORGANISM: Mus musculus

<400> SEQUENCE: 23
ggaatccgag gggttgggtt aaaacttgaa atgg                             34

<210> SEQ ID NO 24
<211> LENGTH: 35
<212> TYPE: DNA
<213> ORGANISM: Mus musculus

<400> SEQUENCE: 24
gagtctccac ccggattcta aagtatatac ccccc                            35

<210> SEQ ID NO 25
<211> LENGTH: 35
<212> TYPE: DNA
<213> ORGANISM: Mus musculus

<400> SEQUENCE: 25
gctttccttt cagcggcgct aataaaatct tgaac                            35

<210> SEQ ID NO 26
<211> LENGTH: 35
<212> TYPE: DNA
<213> ORGANISM: Mus musculus

<400> SEQUENCE: 26
gggggccggg ggcggcggag taaagactac agacc                            35

<210> SEQ ID NO 27
<211> LENGTH: 35
<212> TYPE: DNA
<213> ORGANISM: Mus musculus

<400> SEQUENCE: 27
ggggcgacct cttcctgcga aacgtgaatt ctgag                            35

<210> SEQ ID NO 28
<211> LENGTH: 34
<212> TYPE: DNA
<213> ORGANISM: Mus musculus

<400> SEQUENCE: 28
ggccttctgc caatccagta catttgaaat tacc                             34
```

```
<210> SEQ ID NO 29
<211> LENGTH: 35
<212> TYPE: DNA
<213> ORGANISM: Mus musculus

<400> SEQUENCE: 29
ggtctttctg cggaatccgt ggacattttc ctgcg                                  35

<210> SEQ ID NO 30
<211> LENGTH: 34
<212> TYPE: DNA
<213> ORGANISM: Mus musculus

<400> SEQUENCE: 30
gctctcgaac caggctgcgc gagactgact ggcc                                   34

<210> SEQ ID NO 31
<211> LENGTH: 34
<212> TYPE: DNA
<213> ORGANISM: Mus musculus

<400> SEQUENCE: 31
gctccccaac ccgctcgcgc aaacttttag tacc                                   34
```